US011278060B1

(12) United States Patent
Aradachi

(10) Patent No.: US 11,278,060 B1
(45) Date of Patent: Mar. 22, 2022

(54) INHALER CONTROLLER

(71) Applicant: Japan Tobacco Inc., Tokyo (JP)

(72) Inventor: Takao Aradachi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 17/464,694

(22) Filed: Sep. 2, 2021

(30) Foreign Application Priority Data

Sep. 7, 2020 (JP) .............................. JP2020-150101

(51) Int. Cl.
| | |
|---|---|
| *A24F 40/57* | (2020.01) |
| *H02J 7/00* | (2006.01) |
| *H02J 7/34* | (2006.01) |
| *A24F 40/90* | (2020.01) |
| *A61M 11/04* | (2006.01) |
| *H02M 7/06* | (2006.01) |
| *A24F 40/10* | (2020.01) |
| *A24F 40/20* | (2020.01) |
| *A24F 40/30* | (2020.01) |

(52) U.S. Cl.
CPC .............. *A24F 40/57* (2020.01); *A24F 40/90* (2020.01); *H02J 7/0029* (2013.01); *H02J 7/0048* (2020.01); *H02J 7/00714* (2020.01); *H02J 7/342* (2020.01); *A24F 40/10* (2020.01); *A24F 40/20* (2020.01); *A24F 40/30* (2020.01); *A61M 11/042* (2014.02); *H02J 2207/20* (2020.01); *H02M 7/06* (2013.01)

(58) Field of Classification Search
CPC .......... A24F 40/57; A24F 40/10; A24F 40/30; H02J 7/0048; H02J 7/342; H02J 2207/20; A61M 11/042; H02M 7/06

See application file for complete search history.

(56) References Cited

U.S. PATENT DOCUMENTS

| 5,986,354 A | 11/1999 | Nagao et al. |
| 2007/0235026 A1 | 10/2007 | Hamano |
| 2011/0057724 A1 | 3/2011 | Pabon |
| 2020/0128884 A1* | 4/2020 | Yamada .................. A24F 40/30 |

(Continued)

FOREIGN PATENT DOCUMENTS

| JP | 9-16277 A | 1/1997 |
| JP | 6625258 B1 | 12/2019 |
| JP | 2020-500531 A | 1/2020 |

(Continued)

OTHER PUBLICATIONS

Notice of Reasons for Refusal dated Nov. 27, 2020, received for JP Application 2020-150101, 10 pages including English Translation.

(Continued)

*Primary Examiner* — Jared Fureman
*Assistant Examiner* — Duc M Pham
(74) *Attorney, Agent, or Firm* — Xsensus LLP

(57) ABSTRACT

An inhaler controller includes a first path configured to connect a first voltage terminal to which a first voltage is supplied and a connection terminal to which a heater configured to heat an aerosol source is connected, a second path configured to connect a second voltage terminal to which a second voltage different from the first voltage is supplied and the connection terminal via a resistor, and a measurement circuit configured to measure a resistance value of the heater.

20 Claims, 12 Drawing Sheets

(56) References Cited

U.S. PATENT DOCUMENTS

2020/0375260 A1* 12/2020 Mizuguchi ............ A61M 15/06
2021/0127755 A1* 5/2021 Tatsuta .................. A24F 40/465

FOREIGN PATENT DOCUMENTS

| JP | 2020-68706 A | 5/2020 |
| JP | 6749513 B1 | 9/2020 |
| WO | 2018/100497 A1 | 6/2018 |
| WO | 2020/064347 A1 | 4/2020 |

OTHER PUBLICATIONS

Decision to Grant dated Apr. 12, 2021, received for JP Application 2020-150101, 5 pages including English Translation.
Extended European search report dated Feb. 2, 2022, in corresponding European patent Application No. 21194276.8, 8 pages.

* cited by examiner

INHALER CONTROLLER

CROSS-REFERENCE TO RELATED APPLICATIONS

The present invention contains subject matter related to Japanese Patent Application No. 2020-150101 filed in the Japan Patent Office on Sep. 7, 2020, the entire contents of which is incorporated herein by reference.

BACKGROUND OF THE INVENTION

Field of the Invention

The present invention relates to an inhaler controller.

Description of the Related Art

Japanese Patent Laid-Open No. 2020-500531 discloses an aerosol delivery apparatus including a power supply, a PWM inverter, a constant voltage regulator that supplies a predetermined voltage level to the PWM inverter based on a voltage supplied from the power supply, a resonance transformer driven by the PWM inverter, and a microprocessor.

Recently, an inhaler has been required to have multiple functions. For example, the inhaler incorporates a heating function, a charging function, a communication function, a notification function, a sensor function, a computation function, and the like. On the other hand, the inhaler is required to be compact and have low power consumption. A conventional inhaler is driven by a single voltage converter. When at least one of the devices mounted in the inhaler is to be operated, the voltage converter needs to be activated, and all the devices need to be driven by a common voltage. Accordingly, strict limitations have been imposed on the reduction of power consumption and/or the expansion of multifunctionality.

According to one aspect of the present invention, it is an object to provide an inhaler controller advantageous for the reduction of power consumption and/or the expansion of multifunctionality.

SUMMARY OF THE INVENTION

According to one aspect of the present invention, it is an object to improve the permissivity with respect to a change in voltage supplied to a heater for heating an aerosol source.

One aspect of the present invention provides an inhaler controller comprising: a connection terminal to which a heater configured to heat an aerosol source is connected; a control circuit configured to control an operation of the inhaler controller; a first voltage converter configured to supply a voltage to the control circuit; and a second voltage converter configured to supply a voltage to the connection terminal, wherein a first period in which the first voltage converter operates is different from a second period in which the second voltage converter operates.

The second period can be part of the first period.

The inhaler controller can further comprise: a power supply; a first power supply path configured to supply a voltage from the power supply to the first voltage converter; a second power supply path configured to supply a voltage from the power supply to the second voltage converter; and a third power supply path configured to supply a voltage from an external power supply to the first voltage converter.

The inhaler controller can be configured such that a voltage cannot be supplied from the external power supply to the second voltage converter.

The inhaler controller can be configured such that a first rectifier element is arranged in the first power supply path, and a voltage is supplied from the power supply to the first voltage converter via the first rectifier element.

The first rectifier element can include a Schottky diode.

The inhaler controller can be configured such that a first transistor is connected in parallel with the first rectifier element.

The first transistor can include a first body diode. A forward direction of the first body diode can be the same as a forward direction of the Schottky diode.

The power supply can be charged by the external power supply via the first transistor.

The inhaler controller can be configured such that a second rectifier element is arranged in the third power supply path, and a voltage is supplied from the external power supply to the first voltage converter via the second rectifier element.

The inhaler controller can be configured such that a second rectifier element is arranged in the third power supply path, and a voltage is supplied from the external power supply to the first voltage converter via the second rectifier element, and the second rectifier element includes a second body diode included in a second transistor arranged in the third power supply path.

The inhaler controller can be configured such that a source of the first transistor is electrically connected to a source of the second transistor.

The inhaler controller can be configured such that a source of the first transistor, a source of the second transistor, and a power supply terminal of the first voltage converter are electrically connected to each other.

The power supply can be charged by the external power supply via the first transistor and the second transistor.

The inhaler controller can be configured such that a positive terminal of the power supply is electrically connected to the second voltage converter via the second power supply path.

The inhaler controller can further comprise a regulator configured to supply a voltage to the connection terminal so as to cause the heater to heat the aerosol source.

The inhaler controller can be configured such that the number of loads connected to an output terminal of the first voltage converter can be larger than the number of loads connected to an output terminal of the second voltage converter.

The inhaler controller can be configured such that total power consumption of the loads connected to the output terminal of the first voltage converter is smaller than total power consumption of the loads connected to the output terminal of the second voltage converter.

The inhaler controller can be configured such that self-current consumption of the first voltage converter is smaller than self-current consumption of the second voltage converter.

The inhaler controller can be configured such that a load transient response characteristic of the second voltage converter is better than a load transient response characteristic of the first voltage converter.

DESCRIPTION OF THE EMBODIMENTS

Figure 1:
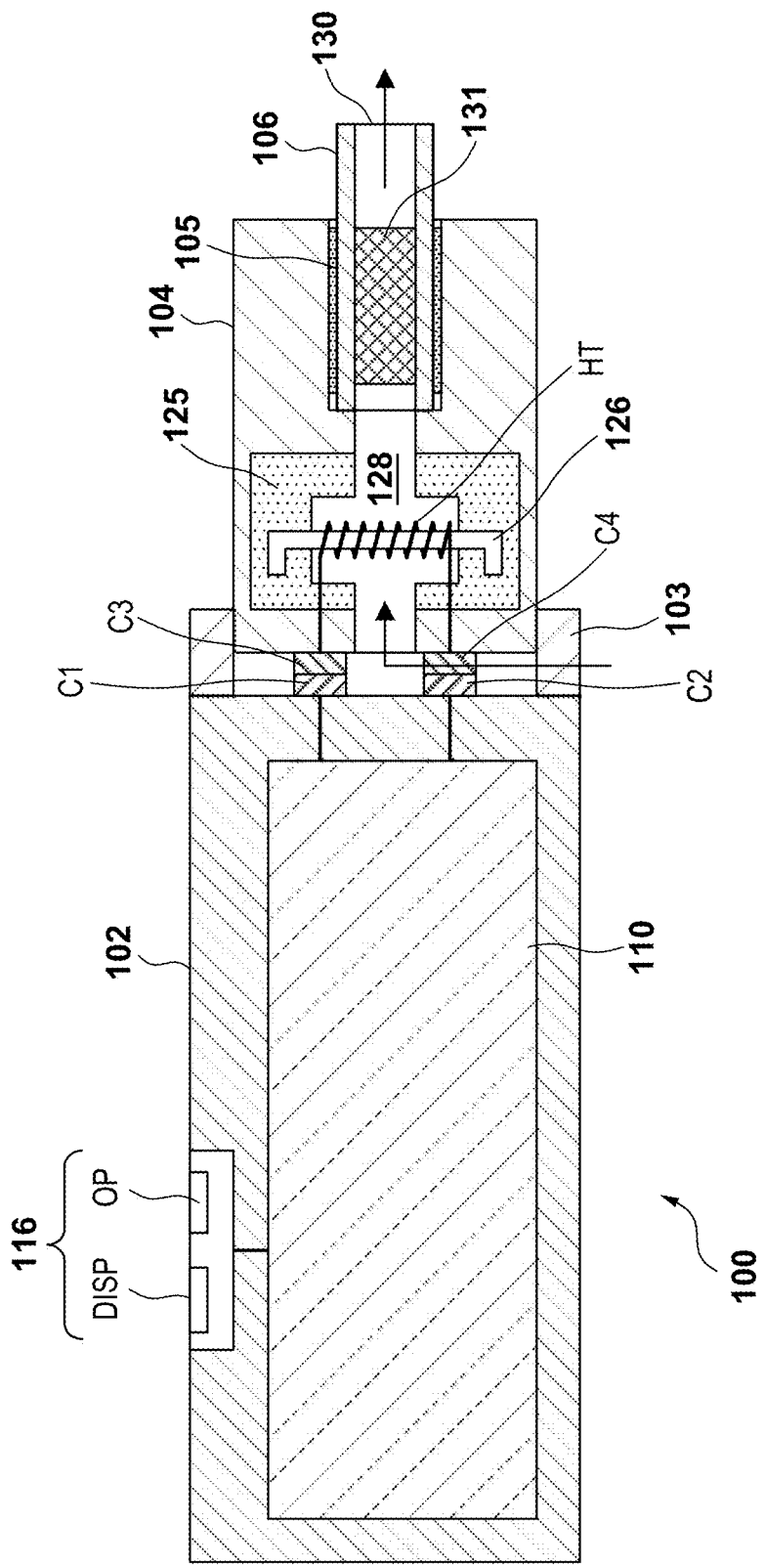
FIG. 1 is a view schematically showing the arrangement of an inhaler according to one embodiment.

Hereinafter, embodiments will be described in detail with reference to the accompanying drawings. It should be noted that the following embodiments are not intended to limit the scope of the appended claims, and that not all the combinations of features described in the embodiments are necessarily essential to the present invention. Of a plurality of features described in the embodiments, two or more features may arbitrarily be combined. In addition, the same reference numerals denote the same or similar parts, and a repetitive description will be omitted.

FIG. 1 schematically shows the arrangement of an inhaler 100 according to an embodiment. The inhaler 100 can be configured as an aerosol generation device. The inhaler 100 can be configured to provide, to a user via a suction port or a mouthpieth 130, a gas containing an aerosol, a gas containing an aerosol and a flavor material, an aerosol, or an aerosol containing a flavor material in accordance with an operation requesting the aerosol (to be also referred to as an aerosol requesting operation hereinafter) such as a suction or inhaling operation by the user. The inhaler 100 can comprise a controller 102 and an atomizer 104. The inhaler 100 can comprise a holding portion 103 that detachably holds the atomizer 104. The controller 102 may be understood as an inhaler controller. The atomizer 104 can be configured to atomize an aerosol source. The aerosol source can be, for example, a liquid such as a multivalent alcohol such as glycerin or propylene glycol. Alternatively, the aerosol source may contain a drug. The aerosol source can be a liquid, a solid, or a mixture of a liquid and a solid. A vapor source such as water may be used in place of the aerosol source.

The inhaler 100 may further comprise a capsule 106 containing a flavor source 131. The atomizer 104 can include a capsule holder 105 that detachably holds the capsule 106. The capsule holder 105 may be included in the controller 102 instead of the atomizer 104. The flavor source 131 can be a molded body obtained by molding, for example, a cigarette material. Alternatively, the flavor source 131 may be made of a plant (for example, mint, herb, Chinese medicine, coffee beans, or the like) except the cigarette. A fragrance such as menthol may be added to the flavor source. The flavor source 131 may be added to an aerosol source. The atomizer 104 and the capsule holder 105 may be integrally formed in place of an arrangement in which the inhaler 100 or the atomizer 104 includes the capsule holder 105.

The controller 102 can include electrical components 110. The electrical components 110 can include a user interface 116. Alternatively, the controller 102 may be understood to include the electrical components 110 and the user interface 116. The user interface 116 can include, for example, a display DISP (for example, an LED (Light Emitting Diode) and/or an image display such as an LCD) and/or an operation unit OP (for example, a switch such as a button switch and/or a touch display). The display DISP may be understood as a notificator that notifies information.

The holding portion 103 of the controller 102 can include a first electrical contact C1 and a second electrical contact C2. In a state in which the atomizer 104 is held by the holding portion 103, the first electrical contact C1 of the holding portion 103 can contact a third electrical contact C3 of the atomizer 104, and the second electrical contact C2 of the holding portion 103 can contact a fourth electrical contact C4 of the atomizer 104. The controller 102 can supply power to the atomizer 104 via the first electrical contact C1 and the second electrical contact C2.

The atomizer 104 can include the third electrical contact C3 and the fourth electrical contact C4 described above. In addition, the atomizer 104 can include a heater HT for heating the aerosol source, a container 125 for holding the aerosol source, and a transport portion (wick) 126 for transporting the aerosol source held by the container 125 to a heating region of the heater HT and holding the aerosol source in the heating region. At least part of the heating region can be arranged in a channel 128 formed in the atomizer 104. The first electrical contact C1, the third electrical contact C3, the heater HT, the fourth electrical contact C4, and the second electrical contact C2 form a current path for flowing the current to the heater HT. The transport portion 126 can be made of a fiber element such as a glass fiber, a porous material such as a ceramic, or a combination thereof. Note that the means for transporting the aerosol source held in the container 125 to the heating region is not limited to the wick, but a spraying device such as a spray or a transporting means such as a pump may be used instead.

As described above, the atomizer 104 can include the capsule holder 105 for detachably holding the capsule 106. As an example, the capsule holder 105 can hold the capsule 106 such that part of the capsule 106 is accommodated in the capsule holder 105 or the atomizer 104 and the remaining part of the capsule 106 is exposed. The user can hold the suction port 130 with his/her mouth and suck the gas containing the aerosol. Since the detachable capsule 106 includes the suction port 130, the inhaler 100 can be kept clean.

When the user holds the suction port 130 with his/her mouth and performs the suction operation, as exemplified by an arrow, air flows into the channel 128 of the atomizer 104 via an opening (not shown). When the heater HT heats the aerosol source, the vaporized and/or aerosolized aerosol source is transported toward the suction port 130 with the air. In the process in which the aerosol source is transported toward the suction port 130, the vaporized and/or aerosolized aerosol source is cooled to form fine liquid droplets, thereby promoting aerosolization. In the arrangement in which the flavor source 131 is arranged, the flavor material generated by the flavor source 131 is added to this aerosol, and the resultant material is transported to the suction port 130, thus allowing the user to suck the aerosol containing the flavor material. Since the flavor material generated by the flavor source 131 is added to the aerosol, the flavor material can be efficiently transported to the lungs of the user without staying in the oral cavity.

Figure 2:
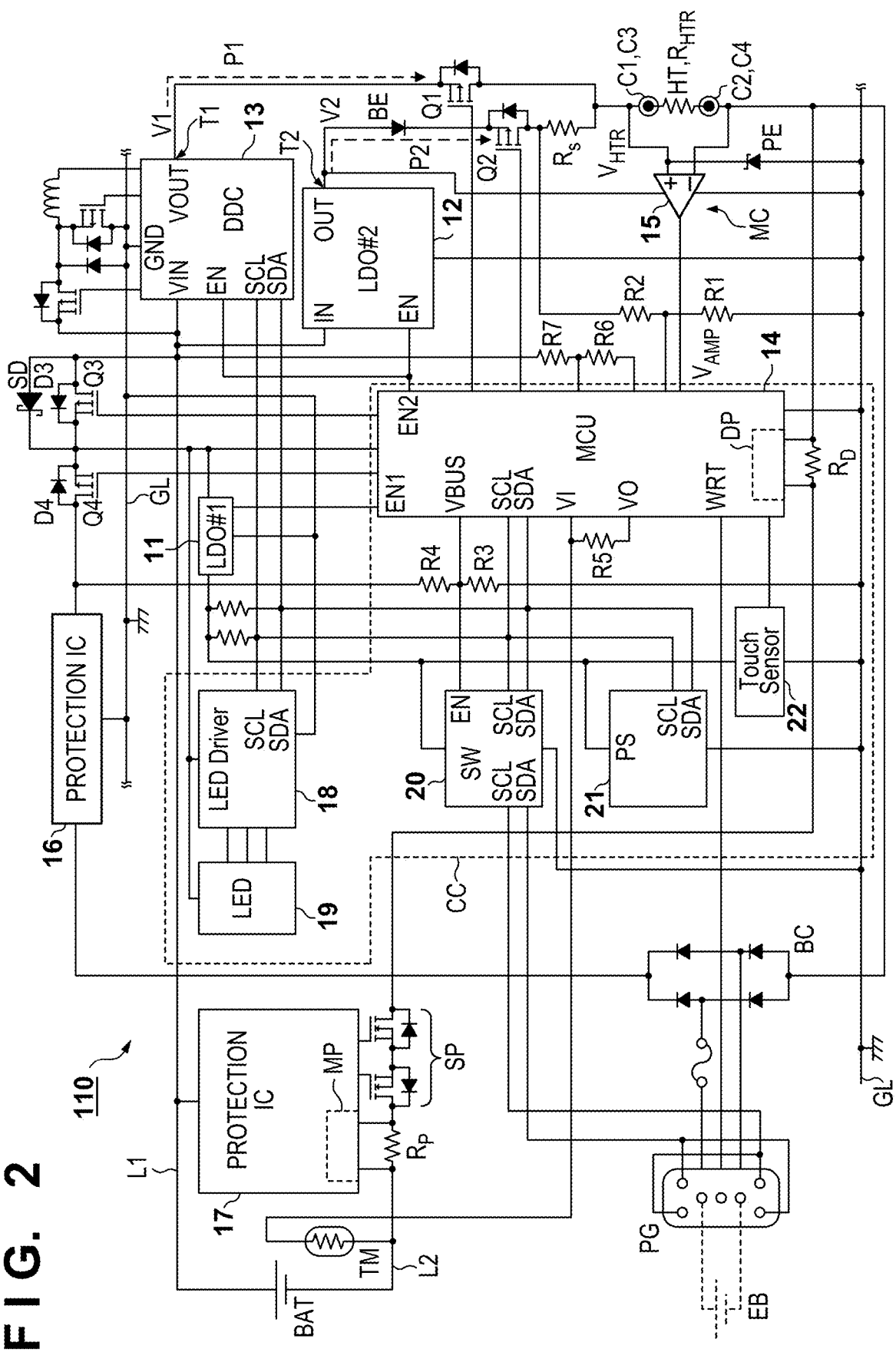
FIG. 2 is a circuit diagram showing an example of the arrangement of the electrical components of a controller in the inhaler shown in FIG. 1.

FIG. 2 shows an example of the arrangement of the electrical components 110 of the controller 102. The electrical components 110 can include, for example, a power supply BAT, protection circuits 16 and 17, a control circuit CC, a first voltage converter 11, a second voltage converter (second regulator) 12, a third voltage converter (first regulator) 13, a first switch Q1, a second switch Q2, a first transistor (third switch) Q3, a second transistor (fourth switch) Q4, a measurement circuit MC, a plug PG, and a bridge circuit BC. Note that a female type (concave type) receptor may be used instead of the male type (convex type) plug PG. The control circuit CC is configured to control the operation of the controller 102. The control circuit CC can include, for example, a processor 14, an LED driver 18, an LED 19, a switch 20, a puff sensor 21, and a touch sensor 22. It is possible to use, as the power supply BAT, for example, a lithium ion secondary battery, a lithium ion capacitor, a combination thereof, or another type of power supply element.

The processor 14 can be formed by, for example, an MCU. The LED driver 18 and the LED 19 can form all or part of the display DISP described above. The LED 19 is an example of a display. The LED driver 18 can drive the LED 19 in accordance with commands from the processor 14. The puff sensor 21 can detect a puff operation by the user. The puff sensor 21 may be formed by, for example, a microphone condenser, a flow rate sensor, or one or a plurality of pressure sensors. The touch sensor 22 can form all or part of the operation unit OP described above. The controller 102 receives the supply of power from an external power supply EB via the plug PG. In addition, the controller 102 can communicate with an external apparatus (not shown) having the external power supply EB via the switch 20 and the plug PG. The processor 14 can communicate with the LED driver 18, the switch 20, the puff sensor 21, and the third voltage converter 13 via a communication interface such as I$^2$C communication as one kind of serial communication using SDA (Serial DAta) lines and SCL (Serial CLock) lines. Note that the communication interface is not limited to I$^2$C communication, but another type of serial communication interface such as UART communication or SPI communication may be used instead. The switch 20 has an enable terminal EN. A voltage obtained by dividing the voltage applied from the external apparatus via the plug PG and the protection circuit 16 by resistors R4 and R3 can be supplied to the enable terminal EN. When the voltage supplied to the enable terminal EN exceeds a predetermined level, the switch 20 can set a connection state (communicable state) between the communication interface among the processor 14, the LED driver 18, the switch 20, the puff sensor 21, and the third voltage converter 13 and the external apparatus connected to the plug PG. According to another point of view, when the voltage supplied to the enable terminal EN exceeds the predetermined level, the switch 20 can set a connection state (communicable state) between the processor 14 and the external apparatus connected to the plug PG.

According to one aspect, the electrical components 110 of the controller 102 can include a first path P1, a second path P2, and the measurement circuit MC. The first path P1 electrically connects a first voltage terminal Ti, to which a first voltage V1 is supplied, to a connection terminal C1, to which the heater HT for heating the aerosol source of the atomizer 104 is connected. The second path P2 electrically connects the connection terminal C1 to a second voltage terminal T2, to which a second voltage V2 different from the first voltage V1 is supplied, via a resistor $R_S$. The measurement circuit MC measures a resistance value $R_{HTR}$ of the heater HT. The first voltage V1 is a voltage for heating the heater HT. The second voltage V2 is a voltage for measuring the resistance value $R_{HTR}$ of the heater HT. If the heater HT has a positive or negative temperature coefficient characteristic that the resistance value $R_{HTR}$ changes in accordance with the temperature of the heater HT itself, the resistance value $R_{HTR}$ of the heater HT has a strong correlation with its temperature. In other words, the processor 14 can acquire the temperature of the heater HT by acquiring the resistance value $R_{HTR}$ of the heater HT using the measurement circuit MC. Controlling the temperature of the heater HT is closely associated with the delivery of an aerosol having an intended flavor from the inhaler 100 to the user, and hence is important. The processor 14 may control a current flowing in the first path P1 based on an output from the measurement circuit MC that measures the resistance value $R_{HTR}$ of the heater HT such that the temperature of the heater HT converges to a target value or target range. In addition, the processor 14 may cut off the current flowing in the first path P1 when the temperature of the heater HT exceeds a threshold based on an output from the measurement circuit MC that measures the resistance value $R_{HTR}$ of the heater HT.

According to this arrangement, even when the first voltage V1 is changed to heat the heater HT, the second voltage V2 for measuring the resistance value $R_{HTR}$ of the heater HT is free from the influence of the change. Accordingly, when the first voltage V1 is changed, the processing of measuring the resistance value $R_{HTR}$ of the heater HT is also free from the influence of the change. That is, it is possible to improve the permissivity with respect to a change in the voltage supplied to the heater HT for heating the aerosol source. The first voltage V1 can be changed in accordance with information representing heating strength as will be described later. Alternatively, the first voltage V1 can be changed by changing the design or usage of the inhaler 100.

For example, the third voltage converter (first regulator) 13 can provide the first voltage V1. The third voltage converter 13 can generate the first voltage V1 by, for example, using the voltage supplied from the power supply BAT. For example, the third voltage converter 13 can be formed by a buck-boost DC/DC converter. The buck-boost DC/DC converter may be formed by an IC chip and several elements (for example, a coil, a transistor, and a diode) connected to the IC chip. The third voltage converter 13 can be, for example, configured to generate the first voltage V1 in accordance with the heating strength (the heating strength of the heater HT with respect to the aerosol source) commanded by the user. In this case, the information representing the heating strength may be provided from the user to the processor 14 via the operation unit OP including the touch sensor 22 or the external apparatus connected to the plug PG. The processor 14 may be configured to transmit a command value indicating a voltage value corresponding to the information to the third voltage converter 13. The information representing the heating strength can be, for example, specified by the user selecting one of a plurality of modes with different heating strengths. The first voltage V1 can be a voltage higher than, for example, 2.5 V but is not limited to this. The third voltage converter 13 may be formed by a boost DC/DC converter or buck DC/DC converter instead of the buck-boost DC/DC converter. In order to implement various heating strengths, the third voltage converter 13 is more preferably formed by a buck-boost DC/DC converter having the broadest range of first voltages V1 that can be generated. Note that the conversion efficiency may be improved or the mounting area may be reduced by forming the third voltage converter 13 using a boost DC/DC converter or buck DC/DC converter depending on the required heating strength or the heater HT to be used.

For example, the second voltage converter (second regulator) 12 can provide the second voltage V2. The second voltage converter 12 can generate the second voltage V2 by, for example, using the voltage supplied from the power supply BAT. The second voltage converter 12 can be formed by, for example, an LDO (Low DropOut). The second voltage V2 can be, for example, 2.5 V but is not limited to this. The second voltage converter 12 may be formed by a switching regulator such as the above DC/DC converter instead of the LDO. Note, however, that the second voltage converter 12 is not required to change the value of the voltage to be generated in accordance with the heating strength unlike the third voltage converter 13, and the fixed second voltage V2 is preferably generated to stably measure the resistance value $R_{HTR}$ of the heater HT. In consideration of this point, because there is no need to use the coil, the transistor, the diode, and the like described above, the second voltage converter 12 may be formed by the LDO that can easily implement a small-size, low-cost converter. Note that since the LDO discards the difference between a voltage (power) supplied and a voltage (power) to be output as heat, it is difficult for the LDO to handle a large current as compared with a DC/DC converter. Since the current flowing in the second path P2 is smaller than the current flowing in the first path P1, the LDO can be used as the second voltage converter 12.

The processor 14 can be configured to control the third voltage converter (first regulator) 13 and the second voltage converter (second regulator) 12 with a common enable signal EN2. In other words, the third voltage converter 13 and the second voltage converter 12 can be simultaneously started, and the operations of the third voltage converter 13 and the second voltage converter 12 can be simultaneously stopped. This arrangement can easily start and stop the third voltage converter 13 and the second voltage converter 12 while suppressing an increase in substrate size and complexity of wirings. Note also that since the timing when the third voltage converter 13 generates the voltage value V1 is close to or the same as the timing when the second voltage converter 12 generates the second voltage V2, synchronizing the operation of the third voltage converter 13 with the operation of the second voltage converter 12 has almost no adverse effect in terms of power consumption.

The measurement circuit MC can include the second path P2 and a shunt resistor $R_S$ connected in series with the heater HT. Unlike the heater HT, the resistance value of the shunt resistor $R_S$ is almost invariant with respect to the temperature. In addition, the measurement circuit MC can include a differential amplifier 15 that detects a voltage $V_{HTR}$ applied to the heater HT. The differential amplifier 15 can be arranged to detect a voltage drop by the heater HT. In this case, the resistance value of the shunt resistor $R_S$ is denoted by $R_S$, which is identical to the reference symbol of the resistor. The differential amplifier 15 can have a first input terminal (for example, a non-inverting input terminal) to which a voltage corresponding to a voltage at the connection terminal C1 is supplied, a second input terminal (inverting input terminal) to which a predetermined voltage is supplied, and an output terminal. A protection element PE can be connected to the first input terminal. For example, the protection element PE can be configured to prevent a voltage exceeding the second voltage V2 from being supplied to the first input terminal. The protection element PE can include, for example, a Zener diode or varistor.

In the second path P2, the second switch Q2 can be arranged in series with the shunt resistor $R_S$ and the heater HT. The electrical components 110 can include, for example, a cutoff unit BE that cuts off the current flowing between the first path P1 and the second path P2 owing to the difference between the voltage value V1 and the second voltage V2. As will be described later, when a period in which the first switch Q1 is ON partly overlap a period in which the second switch Q2 is ON, a current may flow from the first path P1 to the second path P2. For this reason, the cutoff unit BE can protect the second voltage converter 12. The cutoff unit BE can include a rectifier element such as a diode. The rectifier element can be arranged such that the direction from the second voltage terminal T2 to the connection terminal C1 is the forward direction. The second switch Q2 can be controlled by a control signal generated by the processor 14. A voltage can be supplied from the node between the second voltage terminal T2 and the cutoff unit BE to the power supply terminal (voltage receiving terminal) of the differential amplifier 15. The voltage supplied to the power supply terminal of the differential amplifier 15 in this manner is higher by the extent to which the voltage is free from the influence of a drop in the forward voltage of the cutoff unit BE. That is, a different voltage and an output voltage in the differential amplifier 15 become difficult to stick to the voltage supplied to the power supply terminal. In addition, it is possible to improve the resolution of the temperature T of the heater HT acquired by the processor 14 by increasing the amplification factor of the differential amplifier 15 to prevent the differential voltage and the output voltage from sticking to the voltage supplied to the power supply terminal. That is, the processor 14 can acquire the temperature T of the heater HT with high accuracy as compared with the case in which a voltage is supplied from the downstream of the cutoff unit BE to the power supply terminal of the differential amplifier 15 in the direction in which a current flows in the second path P2. In addition, according to the arrangement in which the second voltage converter 12 outputs the second voltage V2 only when the processor 14 acquires the temperature of the heater HT, the differential amplifier 15 operates only when necessary, thereby also implementing the power saving of the inhaler 100. In another point of view, the voltage at the second voltage terminal T2, that is, the second voltage V2, can be supplied to the power supply terminal (voltage receiving terminal) of the differential amplifier 15.

When the resistance value $R_{HTR}$ of the heater HT is detected, the first switch Q1 can be turned off and the second switch Q2 can be turned on. At this time, letting him be a current flowing in the heater HT, $V_{HTR}$ be a voltage at the first connection terminal C1, and $V_f$ be a forward voltage drop at the cutoff unit BE, $R_{HTR}$ is given by equation (1):

$$R_{HTR}=V_{HTR}/I_{HTR}=V_{HTR}\cdot(R_{HTR}+R_S)/(V2-V_f) \qquad (1)$$

Equation (1) is transformed into equation (2) that gives $R_{HTR}$.

$$R_{HTR}=R_S\cdot V_{HTR}/(V2-V_f-V_{HTR}) \qquad (2)$$

Letting $V_{AMP}$ be the output voltage of the differential amplifier 15 and A be the amplification factor of the differential amplifier 15, $V_{AMP}$ is given by equation (3):

$$V_{AMP} = A \cdot V_{HTR} \quad (3)$$

Equation (3) is transformed into equation (4) that gives $R_{HTR}$.

$$V_{HTR} = V_{AMP}/A \quad (4)$$

Therefore, the resistance value $R_{HTR}$ of the heater HT can be obtained according to equations (2) and (4).

The processor 14 can include an input terminal to which the output voltage $V_{AMP}$ of the differential amplifier 15 of the measurement circuit MC is input and an AD converter that converts an analog signal as a voltage input to the input terminal into a digital signal. The processor 14 can generate a control signal that controls the first switch Q1 for controlling heating by the heater HT in accordance with the information ($V_{AMP}$ in this case) obtained by using the measurement circuit MC.

The processor 14 can be formed by, for example, an MCU (Micro Controller Unit). The processor 14 can calculate the temperature of the heater HT according to equation (5) based on the resistance value $R_{HTR}$ of the heater HT.

$$T = T_{ref} + (1/\alpha) \cdot (R_{HTR} - R_{ref}) \cdot (1/R_{ref}) \cdot 10^6 \quad (5)$$

where $T_{ref}$ is a reference temperature, $R_{ref}$ is a reference resistance value, which is the resistance value $R_{HTR}$ of the heater HT at the reference temperature $T_{ref}$, and $\alpha$ is a temperature coefficient [ppm/° C.] of the heater HT. Note that the reference temperature $T_{ref}$ can be set to an arbitrary temperature and is the temperature of the heater HT when the reference resistance value $R_{ref}$ is acquired. As the temperature of the heater HT when the reference resistance value $R_{ref}$ is acquired, the temperature at an arbitrary portion in the inhaler 100 can be used instead. The inhaler 100 can include a temperature sensor (for example, a thermistor TM (to be described later)) that measures a temperature. The temperature measured by the temperature sensor can be set as the reference temperature $T_{ref}$.

Figure 9:
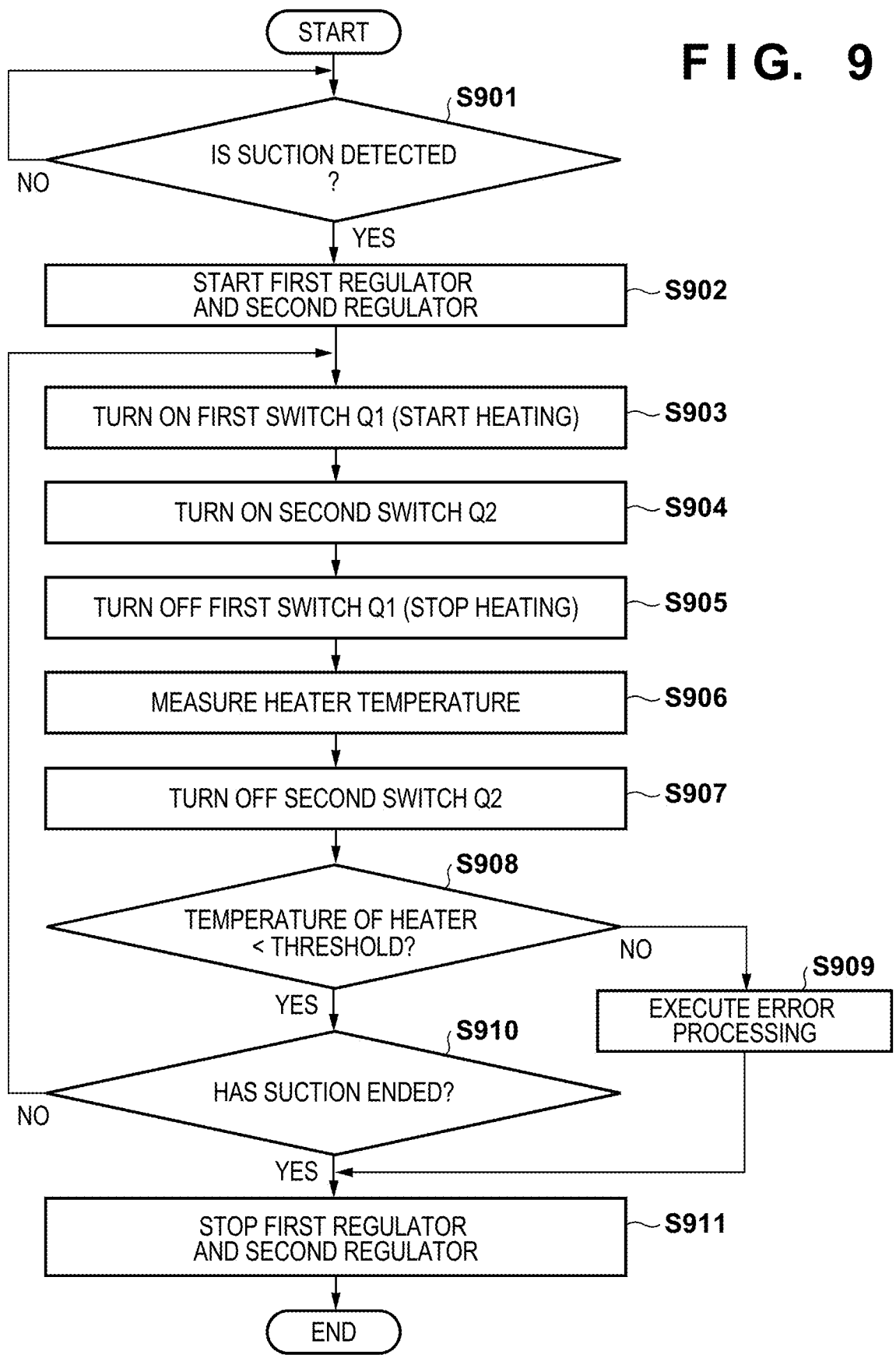
FIG. 9 is a flowchart exemplarily showing temperature control on a heater in the inhaler according to one embodiment.

FIG. 9 shows a procedure for temperature control on the heater HT in the inhaler 100. The processor 14 performs the temperature control shown in FIG. 9. In step S901, the processor 14 can detect suction (puff operation) by the user based on an output from the puff sensor 21. In this case, the puff sensor 21 can be, for example, configured to detect suction (puff operation) by the user based on, for example, at least one of a change in pressure, sound, an air flow, and the operation of the operation unit OP. Upon detecting suction by the user in step S901, the processor 14 starts the third voltage converter (first regulator) 13 and the second voltage converter (second regulator) 12 by activating the enable signal EN2 in step S902. This allows the third voltage converter 13 to output the first voltage V1 from the first voltage terminal T1 and allows the second voltage converter 12 to output the second voltage V2 from the second voltage terminal T2. Note that the first switch Q1 needs to be turned on to cause the third voltage converter 13 to output the voltage value V1 to the first path P1. Likewise, note that the second switch Q2 needs to be turned on to cause the second voltage converter 12 to output the second voltage V2 to the second path P2. This embodiment has exemplified the case in which the puff sensor 21 is used to detect the above aerosol requesting operation. In other words, suction (puff operation) by the user corresponds to an aerosol requesting operation. Instead of this embodiment, the operation unit OP may be used to detect the above aerosol requesting operation. In this case, an operation on the operation unit OP corresponds to the aerosol requesting operation. More specifically, for example, the processor 14 may detect an aerosol requesting operation as long as an operation on the operation unit OP continues.

In step S903, the processor 14 can turn on the first switch Q1. In step S904, the processor 14 can turn on the second switch Q2. In step S905, the processor 14 can turn off the first switch Q1. In step S906, the processor 14 detects the output voltage $V_{AMP}$ of the differential amplifier 15 and can calculate the resistance value Rim of the heater HT according to equations (2) and (4) and the temperature T of the heater HT according to equation (5). Note that the processor 14 may calculate the temperature T of the heater HT according to one equation obtained by solving equations (2), (4), and (5) for the temperature T or may calculate the temperature T of the heater HT according to another method.

In step S907, the processor 14 turns off the second switch Q2. In this case, the processor 14 has a period in which the period during which the first switch Q1 is ON overlaps the period during which the second switch Q2 is ON. However, the processor 14 may control the first switch Q1 and the second switch Q2 so as not to have a period in which the period during which the first switch Q1 is ON overlaps the period during which the second switch Q2 is ON. Having a period in which the period during which the first switch Q1 is ON overlaps the period during which the second switch Q2 is ON allows the processor 14 to calculate the temperature T of the heater HT with high frequency, thereby improving the accuracy of control executed by the processor 14 based on the temperature T of the heater HT. Likewise, this will shorten the period during which the heater HT is not heated upon turning off of the first switch Q1, thereby facilitating delivering an aerosol having an intended flavor to the user.

In step S908, the processor 14 determines whether the temperature T of the heater HT calculated in step S906 is lower than a predetermined temperature (threshold). If the processor 14 determines that the temperature T of the heater HT is lower than the predetermined temperature, the process advances to step S910; otherwise, the processor 14 can execute error processing in step S909. The error processing can include at least one of the following: displaying an error message on the display DISP; inhibiting the heating of the heater HT; waiting for the natural cooling of the heater HT; and analyzing an error cause (for example, specifying an error cause based on the rise rate of the temperature T of the heater HT).

In step S910, the processor 14 determines whether the suction detected in step S901 has ended. If the processor 14 determined that the suction has ended, the process advances to step S911; otherwise, the process returns to step S903. In step S911, the processor 14 stops the operations of the third voltage converter (first regulator) 13 and the second voltage converter (second regulator) 12 by inactivating the enable signal EN2.

When the process returns from step S910 to step S903, the processor 14 can determine the timing (of turning off the first switch Q1) of step S905 thereafter based on the temperature T of the heater HT obtained in preceding step S906. The timing (of turning off the first switch Q1) of step S905 can be determined by, for example, PID computation based on the difference between the target temperature of the heater HT and the temperature T of the heater HT obtained in preceding step S906 such that the temperature T of the heater HT approaches the target temperature.

According to one aspect, the electrical components 110 of the controller 102 can include the connection terminal C1 to which the heater HT for heating the aerosol source of the atomizer 104 is connected, the control circuit CC for controlling the operation of the controller 102, the first voltage converter 11 for supplying a voltage to all or part of the control circuit CC, and the second voltage converter 12 for supplying a voltage (second voltage V2) to the connection terminal C1. In this case, the first period in which the first voltage converter 11 operates can differ from the second period in which the second voltage converter 12 operates. Note that the periods in which the respective voltage converters operate may be interpreted as periods in which voltages converted by starting the respective voltage converters can be output or periods in which the voltages converted by the respective voltage converters are output. In other words, the processor 14 can control the first voltage converter 11 and the second voltage converter 12 such that the first period differs from the second period. The processor 14 can be configured to control the first voltage converter 11 by, for example, using an enable signal EN1. The second period in which the second voltage converter 12 operates can be part of the first period in which the first voltage converter 11 operates. For example, the second period can be started after the start of the first period and before the end of the first period and can be ended before the end of the first period or at the end of the first period. This arrangement allows the processor 14 to separately determine the first period and the second period in accordance with a load (device) to be operated and hence is advantageous in reducing the power consumption of the inhaler 100 or the controller 102.

The first voltage converter 11 can be formed by, for example, an LDO (Low DropOut). In addition, the second voltage converter 12 can be formed by, for example, an LDO (Low DropOut). The first voltage converter 11 and the second voltage converter 12 may have the same specifications or have different specifications. The former case can contribute to a reduction in the manufacturing cost of the controller 102 (the sourcing cost of components). The latter case enables the selection of loads (devices) requiring different performances concerning, for example, power supply voltage, and hence is advantageous in expanding the functionality of the inhaler 100 or the controller 102.

A more specific example of the latter case is that the number of loads connected to the output terminal of the first voltage converter 11 is larger than the number of loads connected to the output terminal of the second voltage converter 12. In the example shown in FIG. 2, the loads connected to the output terminal of the first voltage converter 11 include the switch 20, the puff sensor 21, and the touch sensor 22, whereas the loads connected to the output terminal of the second voltage converter 12 include the second path P2 (heater HT) and the differential amplifier 15. In the example shown in FIG. 2, the LED driver 18 and the LED 19 are not connected to the output terminal of the second voltage converter 12 but are connected to the external power supply EB via the power supply BAT or the plug PG. In another example, the loads connected to the output terminal of the first voltage converter 11 can include the LED driver 18, the LED 19, the switch 20, the puff sensor 21, and the touch sensor 22, whereas the loads connected to the output terminal of the second voltage converter 12 can include the second path P2 (heater HT) and the differential amplifier 15.

Alternatively, the total power consumption of the loads connected to the output terminal of the first voltage converter 11 is lower than the total power consumption of the loads connected to the output terminal of the second voltage converter 12. For example, in the example shown in FIG. 2, the total power consumption of the switch 20, the puff sensor 21, and the touch sensor 22 connected to the output terminal of the first voltage converter 11 is lower than the total power consumption of the heater HT and the differential amplifier 15 connected to the output terminal of the second voltage converter 12. This can be understood in consideration of the main use of the inhaler 100 that delivers an aerosol having a flavor, more specifically, in consideration of the fact that the power consumption of the heater HT is high.

Alternatively, the self-current consumption of the first voltage converter 11 is lower than the self-current consumption of the second voltage converter 12. The self-current consumption of the voltage converter indicates the current consumed by the voltage converter to convert the voltage (power) input to the input terminal of the voltage converter into the voltage (power) output from the output terminal of the voltage converter. The self-current consumption can be referred from the data sheet of the voltage converter. The self-current consumption generally varies in accordance with the specifications of voltage converters. A lower self-current consumption indicates more efficient voltage conversion. That is, a voltage converter with a lower self-current consumption leads to the power saving of the power supply BAT and can suppress the heating of the voltage converter. In particular, when the first period in which the first voltage converter 11 operates is long (as compared with the second period in which the second voltage converter 12 operates), using a voltage converter with a low self-current consumption as the first voltage converter 11 is important in terms of power saving and suppressing the generation of heat. In particular, the inhaler 100 that has achieved power saving increases the amount of aerosol having a flavor that can be provided per charging of the power supply BAT, and hence can greatly improve its commodity value.

Alternatively, the load transient response characteristic of the second voltage converter 12 may be superior to the load transient response characteristic of the first voltage converter 11. The load transient response characteristic of a voltage converter is an index indicating how much time it takes for an output voltage set in a transient state upon an abrupt increase or decrease in the output current of the voltage transfer to be set in a steady state. A load transient response characteristic is generally represented on the voltage basis. A smaller load transient response characteristic indicates that a steady state is set faster. This load transient response characteristic is especially important for a voltage converter that outputs a current or voltage only at the limited timing of acquiring the temperature T of the heater HT as in the first voltage converter 11. This is because, if the load transient response characteristic is not excellent, when the resistance value $R_{HTR}$ (the temperature T of the heater HT) of the heater HT is to be acquired according to equation (2), the second voltage V2 output from the second voltage converter 12 is difficult to exhibit a steady value and it is necessary to keep the second voltage converter 12 active until the second voltage V2 exhibits a steady value. In other words, using the second voltage converter 12 having an excellent load transient response characteristic allows the processor 14 to acquire the resistance value $R_{HTR}$ (the temperature T of the heater HT) of the heater HT fast and accurately and can shorten the period during which the second voltage converter 12 operates, thereby achieving the power saving of the inhaler 100.

The self-current consumption and the load transient response characteristic of a general voltage converter tend to have a trade-off relationship. A voltage converter with a low self-current consumption tends to have a poor load transient response characteristic. In addition, a voltage converter with an excellent load transient response characteristic tends to have a high self-current consumption. Accordingly, it is important how to deal with this trade-off in accordance with the applications of voltage converters and the loads to be connected to the output terminals. In this embodiment, although a large number of loads are connected to the output terminal of the first voltage converter 11, the total power consumption is low and hence does not easily change abruptly. Since it is difficult for an output voltage to make a transition to a transient state, the requirement for an excellent load transient response characteristic is low with respect to the first voltage converter 11. In contrast to this, if the first period in which the first voltage converter 11 operates is long (as compared with the second period in which the second voltage converter 12 operates), the requirement for an excellent load transient response characteristic is high with respect to the first voltage converter 11. That is, the first voltage converter 11 is preferably formed by a voltage converter with a low self-current consumption even if its load transient response characteristic is not excellent.

In this embodiment, although a small number of loads are connected to the output terminal of the second voltage converter 12, the total power consumption is high and hence easily changes abruptly. Since an output voltage easily makes a transition to a transient state, the requirement for an excellent load transient response characteristic is high with respect to the first voltage converter 11. In contrast to this, if the second period in which the second voltage converter 12 operates is long (as compared with the first period in which the first voltage converter 11 operates), the requirement for an excellent load transient response characteristic is low with respect to the second voltage converter 12. That is, the second voltage converter 12 is preferably formed by a voltage converter with an excellent load transient response characteristic even if the self-current consumption is high.

In other words, the first voltage converter 11 is preferably formed by a voltage converter that is lower in self-current consumption than the second voltage converter 12 and inferior in load transient response characteristic to the second voltage converter 12. The second voltage converter 12 is preferably formed by a voltage converter that is lower in self-current consumption than the first voltage converter 11 and superior in load transient response characteristic to the first voltage converter 11. In addition, the self-current consumption of the first voltage converter 11 is preferably lower than the self-current consumption of the second voltage converter 12. The load transient response characteristic of the second voltage converter 12 is preferably superior to the load transient response characteristic of the first voltage converter 11.

Figure 3:
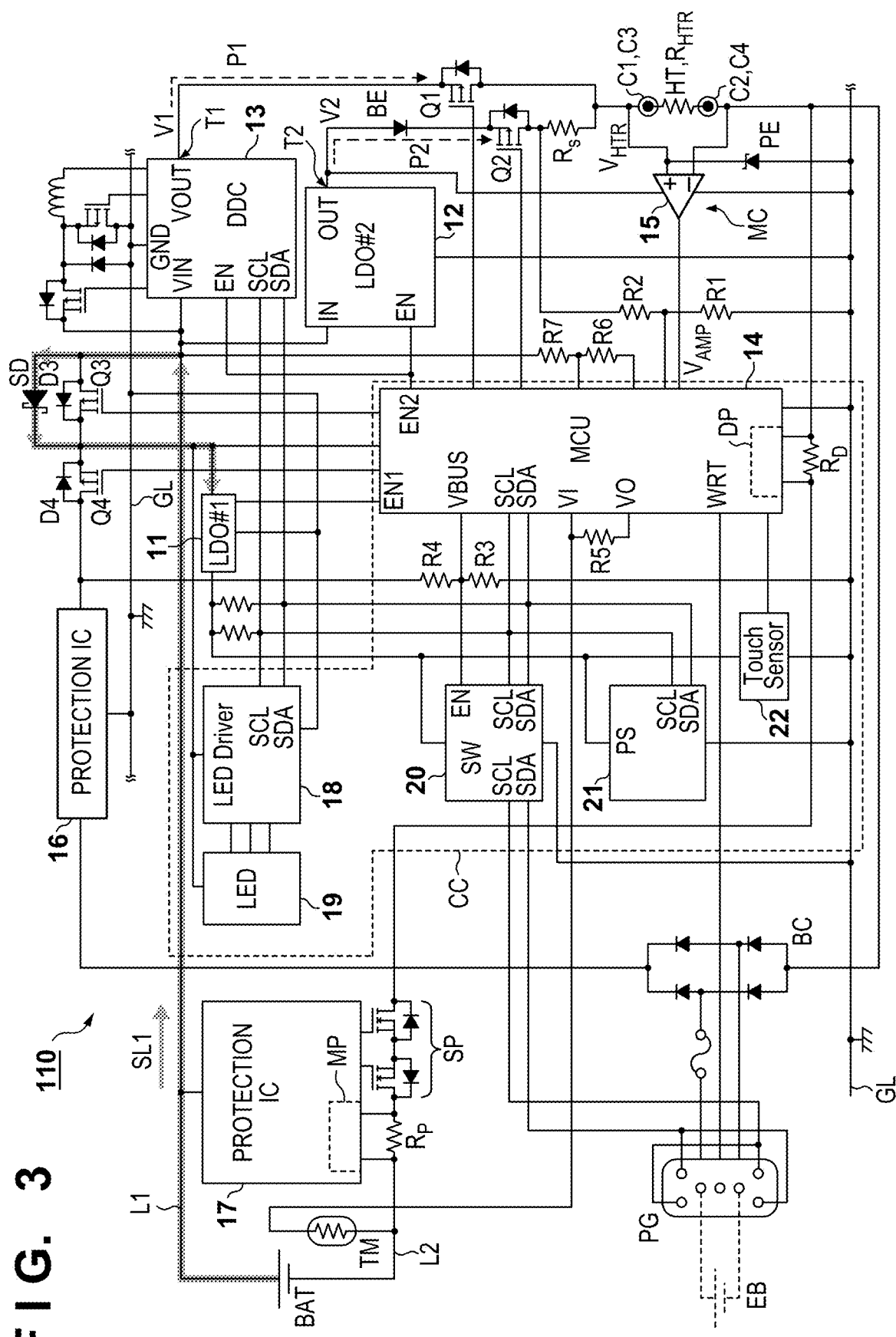
FIG. 3 is a circuit diagram for explaining the arrangement and operation of the electrical components in FIG. 2.
Figure 4:
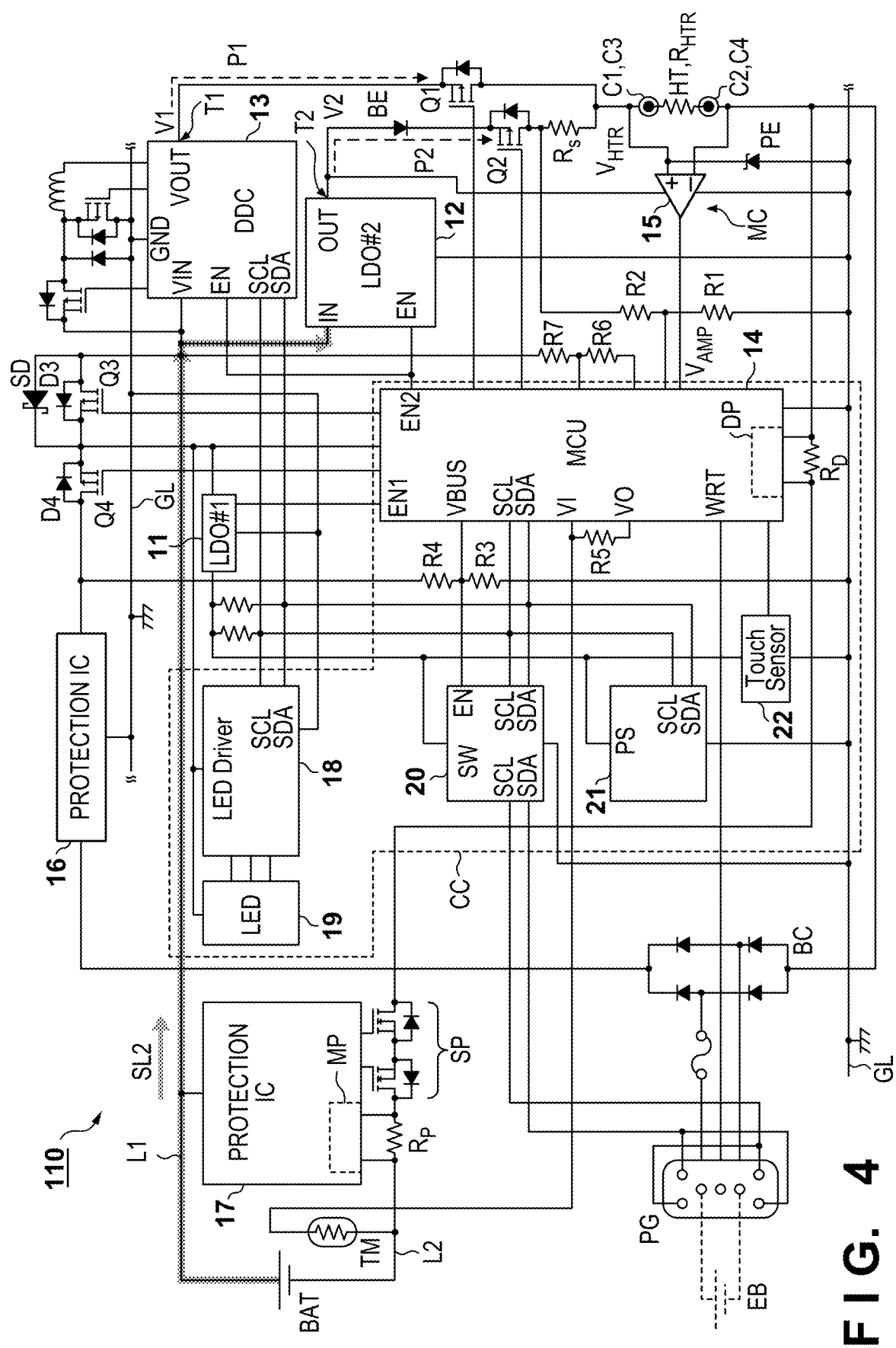
FIG. 4 is a circuit diagram for explaining the arrangement and operation of the electrical components in FIG. 2.
Figure 5:
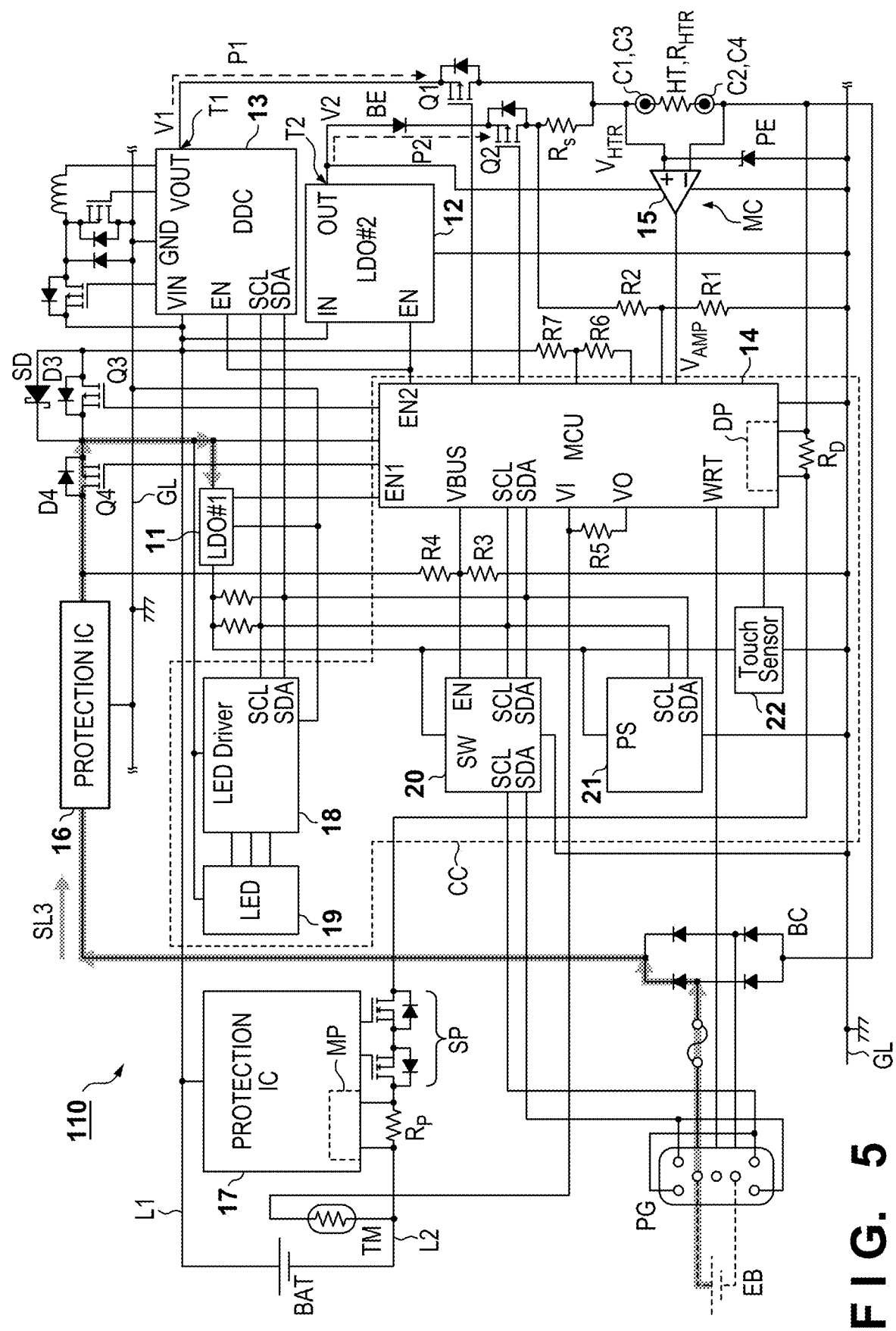
FIG. 5 is a circuit diagram for explaining the arrangement and operation of the electrical components in FIG. 2.

As exemplarily shown in FIGS. 3, 4, and 5, the controller 102 can include a first power supply path SL1 for supplying a voltage from the power supply BAT to the first voltage converter 11, a second power supply path SL2 for supplying a voltage from the power supply BAT to the second voltage converter 12, and a third power supply path SL3 for supplying a voltage from the external power supply EB to the first voltage converter 11. In one point of view, power can be supplied from both the power supply BAT and the external power supply EB to the first voltage converter 11, whereas no power is supplied from the external power supply EB to the second voltage converter 12 even though power can be supplied from the power supply BAT. This can suppress a deterioration in the power supply BAT, which is charged with power supplied from the external power supply EB, caused when the heat generated upon the operation of the second voltage converter 12 and the heater HT is applied to the power supply BAT.

As exemplarily shown in FIG. 3, a first rectifier element SD may be arranged in the first power supply path SL1, and a voltage can be supplied from the power supply BAT to the first voltage converter 11 via the first rectifier element SD. The first rectifier element SD can be arranged such that the direction from the power supply BAT to the first voltage converter 11 is the forward direction. The first rectifier element SD can be, for example, a Schottky diode. The Schottky diode uses contact between a semiconductor and a metal and is smaller in forward voltage drop than a PN junction diode, and hence is advantageous in supplying a voltage from the power supply BAT to the first voltage converter 11. More specifically, supplying a voltage from the power supply BAT to the first voltage converter 11 via the Schottky diode SD will reduce the loss of power supplied from the power supply BAT as compared with supplying a voltage from the power supply BAT to the first voltage converter 11 via a first body diode D3 of the first transistor Q3 (to be described later).

As exemplarily shown in FIG. 4, the positive terminal of the power supply BAT can be electrically connected to the second voltage converter 12 via the second power supply path SL2. The positive terminal of the power supply BAT can be directly connected to the second voltage converter 12 by using a conductive pattern (conductive trace). In another point of view, the positive terminal of the power supply BAT can be electrically connected to the second voltage converter 12 without via any electrical elements such as a resistor, a switch, and an IC. The positive terminal of the power supply BAT can also be electrically connected to the third voltage converter 13 via the second power supply path SL2. This makes it possible to supply power from the power supply BAT to the second voltage converter 12 and the third voltage converter 13 with minimum loss of power.

The first transistor Q3 can be connected in parallel with the first rectifier element SD. The first transistor Q3 can include the first body diode D3. The forward direction of the first body diode D3 can be the same as the forward direction of the first Schottky diode SD. The power supply BAT can be charged by the external power supply EB via the first transistor Q3.

As exemplarily shown in FIG. 5, a second rectifier element D4 can be arranged in the third power supply path SL3. A voltage can be supplied from the external power supply EB to the first voltage converter 11 via the second rectifier element D4. The second rectifier element D4 can include the second body diode provided for the second transistor Q4 arranged in the third power supply path SL3. With this arrangement, the voltage supplied from the external power supply EB undergoes a forward voltage drop by the second rectifier element D4 and is supplied to the input terminal of the first voltage converter 11. When the first voltage converter 11 is formed by a series regulator such as an LDO, an input voltage is stepped down by discarding extra power as heat and output from the output terminal. For this reason, reducing the difference between an input voltage and an output voltage can further suppress the generation of heat by the first voltage converter 11. That is, since a forward voltage drop in the second rectifier element D4 steps down the input voltage of the first voltage converter 11, the generation of heat by the first voltage converter 11 can be suppressed. In other words, since it is possible to prevent the generation of heat from concentrating in the first voltage converter 11 and disperse the generation of heat to the second rectifier element D4 and the first voltage converter 11, the durability of the inhaler 100 can be improved. After the voltage supplied from the external power supply EB via the second rectifier element D4 is supplied to the input terminal of the first voltage converter 11, the processor 14 may turn on the second transistor Q4 and turn on/off the first transistor Q3. This can supply the voltage stepped down by the first transistor Q3 and the Schottky diode SD to the input terminal of the first voltage converter 11 while suppressing the generation of heat in the second rectifier element D4, thereby improving the durability of the inhaler 100.

Figure 6:
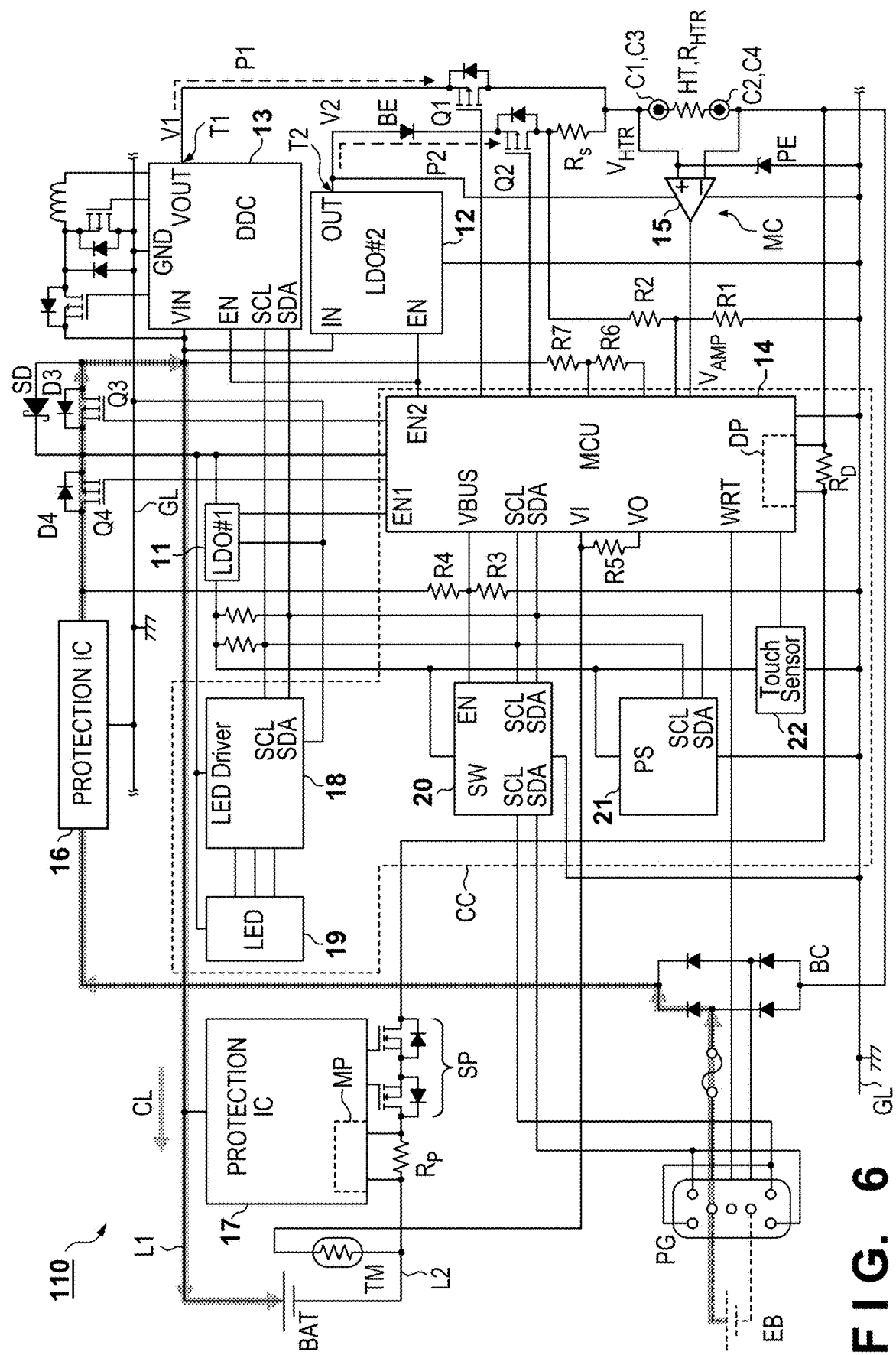
FIG. 6 is a circuit diagram for explaining the arrangement and operation of the electrical components in FIG. 2.

The source of the first transistor Q3 can be electrically connected to the source of the second transistor Q4. In addition, the source of the first transistor Q3 can be electrically connected to the source of the second transistor Q4 and the power supply terminal (power receiving terminal) of the first voltage converter 11. As exemplarily shown in FIG. 6 as a charging path CL, the power supply BAT can be charged by the external power supply EB via the first transistor Q3 and the second transistor Q4. The second transistor Q4 can supply a voltage obtained by stepping down the voltage output from the protection circuit 16 to the first transistor Q3. The first transistor Q3 and the second transistor Q4 can form a charging circuit that charges the power supply BAT. This can disperse the heat generated in the charging circuit to the first transistor Q3 and the second transistor Q4 and hence can improve the durability of the inhaler 100. The first transistor Q3 and the second transistor Q4 can be connected in series with the path in which a charging current flows. The processor 14 can charge the power supply BAT by turning on the second transistor Q4 and turning on or on/off the first transistor Q3. The processor 14 can control the charging of the power supply BAT at high speed by switching on and off the second transistor Q4 at high speed. The charging path CL extends, for example, from the external power supply EB to the positive electrode of the power supply BAT via the plug PG, the bridge circuit BC, the protection circuit 16, the second transistor Q4, and the first transistor Q3.

Figure 7:
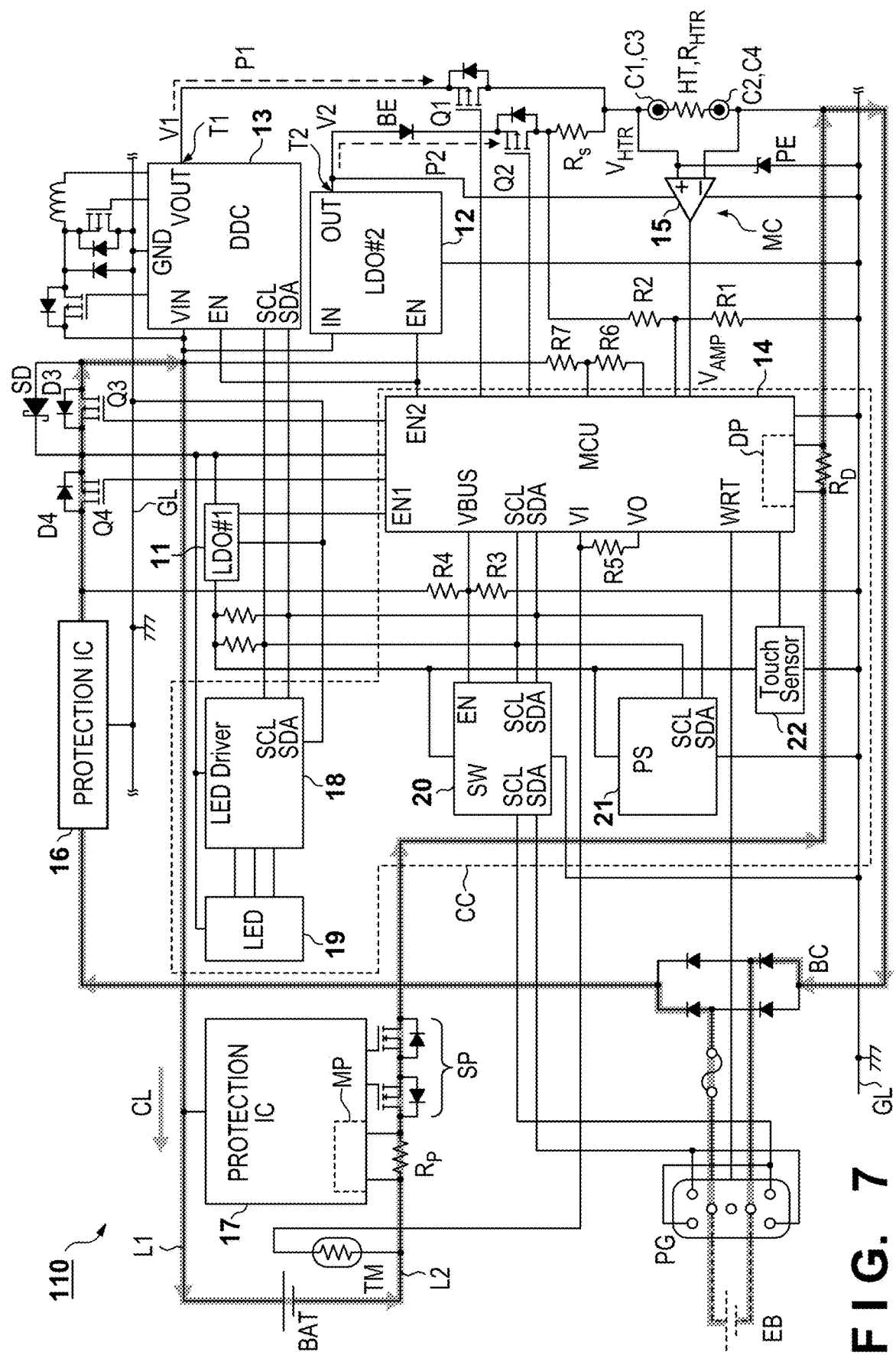
FIG. 7 is a circuit diagram for explaining the arrangement and operation of the electrical components in FIG. 2.
Figure 8:
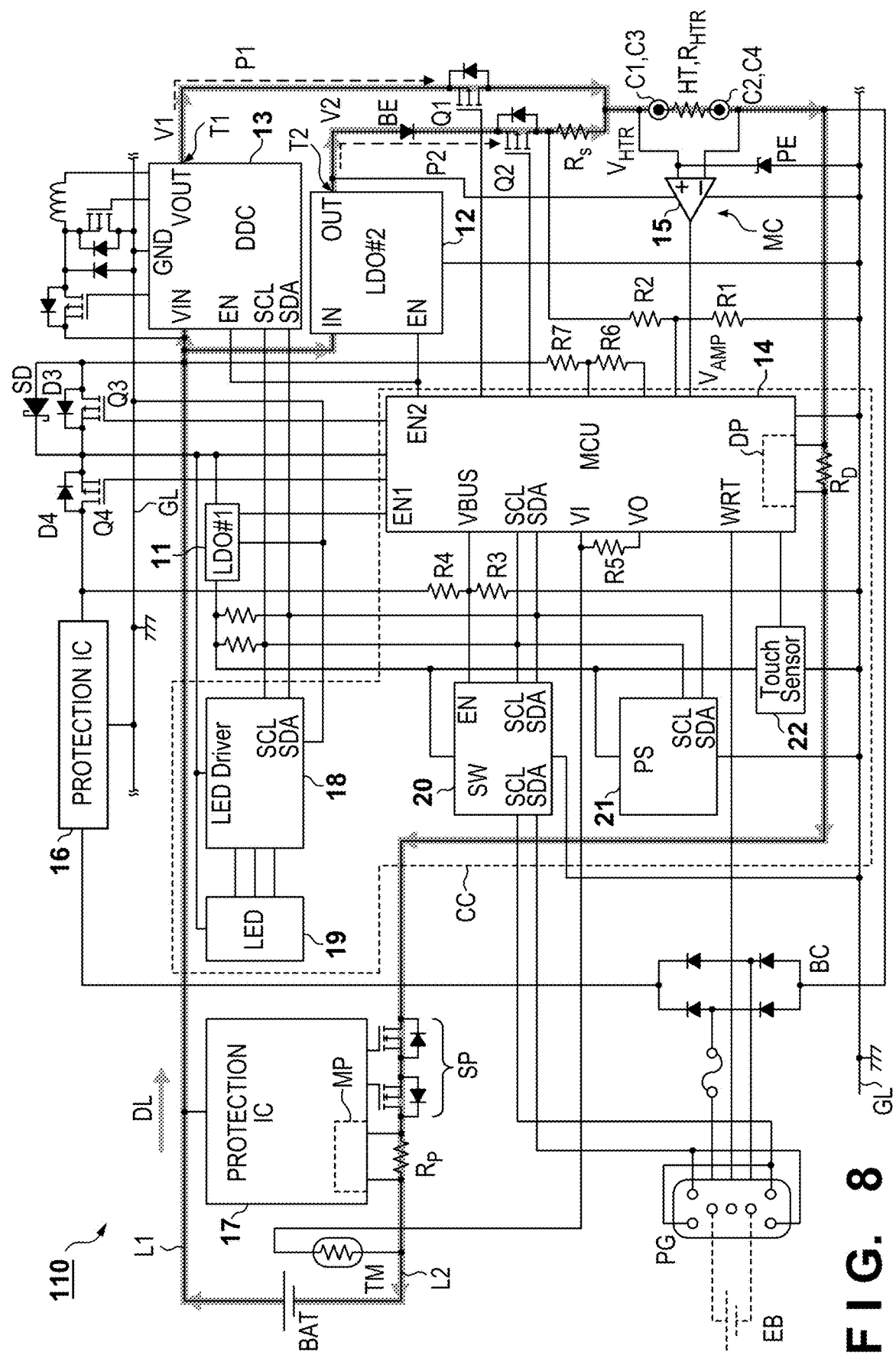
FIG. 8 is a circuit diagram for explaining the arrangement and operation of the electrical components in FIG. 2.

Referring to FIG. 7, the current path (the charging path CL) in a state in which the power supply BAT is charged is indicated by the gray arrows. Referring to FIG. 8, the current path (a discharge path DL) in a state in which the power supply BAT is discharged via the heater HT is indicated by the gray arrows. The controller 102 includes a first line L1 connected to the positive electrode of the power supply BAT and a second line L2 connected to the negative electrode of the power supply BAT. The first line L1 and the second line L2 can be arranged to form part of a closed circuit including the power supply BAT as a constituent element.

In one aspect, the electrical components 110 of the controller 102 can include the power supply BAT, the connection terminal C1 to which the heater HT for heating the aerosol source of the atomizer 104 by using a current supplied from the power supply BAT is connected, the processor 14, and the protection circuit 17. The processor 14 includes a detector DP that detects a current supplied from the power supply BAT and/or a current supplied to the power supply BAT and can control the state of the power supply BAT based on the detection result obtained by the detector DP. The protection circuit 17 includes a monitor MP that monitors the state of the power supply BAT and can protect the power supply BAT based on the monitoring result obtained by the monitor MP. The protection circuit 17 can be provided separately from the processor 14. This arrangement is advantageous in improving the protection function of the power supply BAT and also the protection function of the inhaler 100.

The processor 14 can control the charging of the power supply BAT based on the detection result obtained by the detector DP when the detector DP detects a current supplied to the power supply BAT. More specifically, the processor 14 can control the first transistor Q3 and the second transistor Q4 described above, which form a charging circuit for charging the power supply BAT, based on the detection result obtained by the detector DP. In addition, when the detection result obtained by the detector DP indicates abnormality, the processor 14 can stop charging the power supply BAT using the charging circuit (the first transistor Q3 and the second transistor Q4). For example, when the detection result obtained by the detector DP indicates abnormality, the processor 14 can control the first transistor Q3 into the OFF state. When the first transistor Q3 is set in the OFF state, the electrical connection between the external power supply EB and the power supply BAT is cut off to stop charging the power supply BAT.

The third voltage converter (first regulator) 13 receives the voltage supplied from the power supply BAT and generates the first voltage V1 (driving voltage) for driving the heater HT so as to heat the aerosol source of the atomizer 104. The second voltage converter (second regulator) 12 receives the voltage supplied from the power supply BAT and generates the second voltage V2 (measurement voltage) for measuring the resistance value $R_{HTR}$ of the heater HT. When the detector DP detects the current supplied from the power supply BAT and the detection result obtained by the detector DP indicates abnormality, the processor 14 can stop the operation of the third voltage converter (first regulator) 13 and the second voltage converter (second regulator) 12 by inactivating the enable signal EN2. Alternatively, when the detector DP detects the current supplied from the power supply BAT and the detection result obtained by the detector DP indicates abnormality, the processor 14 may control the first switch Q1 in the OFF state or control the first switch Q1 and the second switch Q2 in the OFF state. Alternatively, the detector DP detects the current supplied from the power supply BAT and the detection result obtained by the detector DP indicates abnormality, the processor 14 controls the first switch Q1 and the second switch Q2 in the OFF state while inactivating the enable signal EN2. In either case, the electrical connection between the power supply BAT and the heater HT is cut off, and hence discharging from the power supply BAT to the heater HT is stopped. The mode of stopping discharging from the power supply BAT to the heater HT by inactivating the enable signal EN2 also stops the operation of the third voltage converter 13 and the second voltage converter 12, and hence is advantageous in power saving of the power supply BAT. The mode of stopping discharging to the heater HT of the power supply BAT by controlling the first switch Q1 and the second switch Q2 in the OFF state is advantageous in terms of the speed of stopping the discharging because of small frequencies of current and voltage transient responses as compared with the case of stopping the operations of the third voltage converter 13 and the second voltage converter 12. The mode of stopping discharging to the heater HT of the power supply BAT by using both the inactivation of the enable signal EN2 and control on the first switch Q1 and the second switch Q2 in the OFF state is advantageous in terms of the capability to stop the discharging at high probability even when either the voltage converter or the switch has failed. When the detection result obtained by the detector DP indicates an overcurrent and the processor 14 handles the corresponding state as abnormality, a short-circuit may have occurred in one of the following: the first switch Q1, the second switch Q2, the third voltage converter 13, and the second voltage converter 12. For this reason, in order to reliably stop discharging to the heater HT of the power supply BAT, it is important to perform both the inactivation of the enable signal EN2 and control on the first switch Q1 and the second switch Q2 in the OFF state.

The protection circuit 17 can include a switch SP arranged in the second line L2 so as to be able to cut off the second line L2. The switch SP is preferably formed by directly connecting two switches in different directions so as to be able to cut off a charging current for charging the power supply BAT and a discharge current discharged from the power supply BAT. When the monitoring result obtained by the monitor MP indicates abnormality, the protection circuit 17 can cut off a current supplied from the power supply BAT and a current supplied to the power supply BAT by turning off the switch SP. The protection circuit 17 receives power from the first line L1.

The detector DP includes a first resistor RD. The monitor MP includes a second resistor $R_P$. The first resistor RD and the second resistor $R_P$ can be arranged in series with a path extending from the positive electrode of the power supply BAT to its negative electrode. The first resistor RD and the second resistor $R_P$ can be arranged to cause a current flowing from the positive electrode of the power supply BAT to pass through the heater HT first and then pass through the first resistor RD and the second resistor $R_P$. Alternatively, the first resistor RD and the second resistor $R_P$ can be arranged in series with the second line L2 (that is, so as to form part of the second line L2). High-side connection can be made between the first resistor RD and the second resistor $R_P$ instead of such low-side connection between the first resistor RD and the second resistor $R_P$. In the high-side connection, the first resistor RD and the second resistor $R_P$ can be arranged to cause a current flowing out from the positive electrode of the power supply BAT to pass through the first resistor RD and the second resistor $R_P$ before passing through the heater HT. Alternatively, the first resistor RD and the second resistor $R_P$ can be arranged in series with the first line L1 (that is, so as to form part of the first line L1). This indicates that when the detector DP or the monitor MP includes a differential amplifier (operational amplifier), the common mode voltage of the differential amplifier can be set low or 0. A lower common mode voltage increases the number of options for differential amplifiers, and hence is advantageous in terms of cost.

The detector DP detects a current flowing in the first resistor RD or a voltage drop caused by the first resistor RD. The processor 14 can detect abnormality based on the detection result obtained by the detector DP and stop the charging of the power supply BAT and/or discharging from the power supply BAT to the heater HT. The monitor MP can detect a current flowing in the second resistor $R_P$ or a voltage drop caused by the second resistor $R_P$. The protection circuit 17 can detect abnormality based on the monitoring result obtained by the monitor MP and stop the charging of the power supply BAT and/or discharging from the power supply BAT to the heater HT.

The condition by which the processor 14 stops the charging of the power supply BAT can differ from the condition by which the protection circuit 17 stops the charging of the power supply BAT. In addition, the condition by which the processor 14 stops charging from the power supply BAT can differ from the condition by which the protection circuit 17 stops charging from the power supply BAT.

The controller 102 can include the thermistor TM having one terminal connected between the negative electrode of the power supply BAT and the switch SP in the second line L2. The thermistor TM is mainly used to acquire the temperature of the power supply BAT. The other terminal of the thermistor TM can be arranged to supply a voltage dependent on the resistance value of the thermistor TM to the processor 14. For example, the processor 14 supplies a predetermined voltage from an output terminal VO to the thermistor TM via a resistor R5 and receives the voltage divided by the resistor R5 and the thermistor TM at an input terminal VI, thereby detecting the resistance value of the thermistor TM. The resistance value of the thermistor TM can provide information indicating a temperature. When the thermistor TM is provided at this position, the output terminal VO is connected to the thermistor TM via the resistor R5 and is then connected to the negative electrode of the power supply BAT via the thermistor TM without via another element. This makes it difficult for noise to mix with a voltage input to the input terminal VI and allows the processor 14 to acquire the temperature of the thermistor TM or the power supply BAT with high accuracy.

Figure 10:
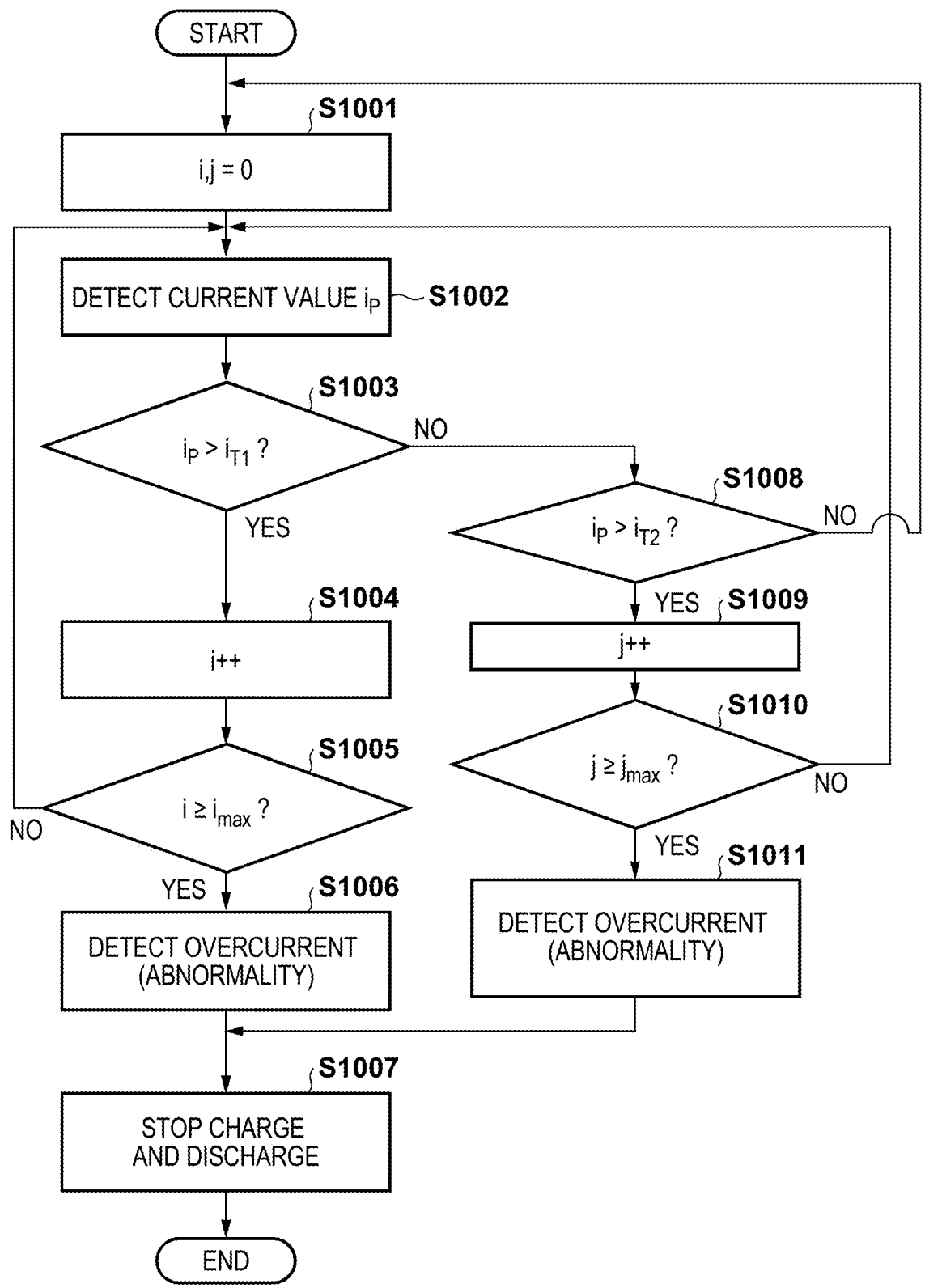
FIG. 10 is a flowchart exemplarily showing the operation of a protection circuit associated with the protection of a power supply.

FIG. 10 exemplarily shows the operation of the protection circuit 17. In step S1001, the protection circuit 17 initializes parameters i and j to 0. In step S1001, the protection circuit 17 detects a current value $i_P$ (a charging current value at the time of charging or a discharge current value at the time of discharging) flowing in the power supply BAT by the monitor MP. In the following description, the current value $i_P$ is handled as an absolute value. Note that at both the time of charging and the time of discharging, the current value $i_P$ indicates only a positive value, and its minimum value is 0. In step S1003, the protection circuit 17 determines whether the current value $i_P$ exceeds a first threshold $i_{T1}$. If YES in step S1003, the process advances to step S1004; otherwise, the process advances to step S1008. In detection signal step S1004, the protection circuit 17 adds 1 to the value of the parameter i. In step S1005, the protection circuit 17 determines whether the value of the parameter i is equal to or more than $i_{max}$. If the value of the parameter i is equal to or more than $i_{max}$, the process advances to step S1006; otherwise, the process returns to step S1002. In this case, that the value of the parameter i is equal to or more than i max indicates that the period during which the current value $i_P$ has exceeded the first threshold $i_{T1}$ has reached a first time t1 ($=i_{max}/f_P$). Note that $f_P$ is the period (sampling period) during which step S1002 is executed. In step S1006, the protection circuit 17 determines that an overcurrent (that is, abnormality) is detected, and the process advances to step S1007.

In step S1008, the protection circuit 17 determines whether the current value $i_P$ exceeds a second threshold $i_{T2}$ smaller than the first threshold $i_{T1}$. If YES in step S1008, the process advances to step S1009; otherwise, the process returns to step S1001. In step S1009, the protection circuit 17 adds 1 to the value of the parameter j. In step S1010, the protection circuit 17 determines whether the value of the parameter j is equal to or more than $j_{max}$. If the value of the parameter j is equal to or more than j max, the process advances to step S1011; otherwise, the process returns to step S1002. In this case, that the value of the parameter j is equal to or more than j max indicates that the period during which the current value $i_P$ has exceeded the second threshold $i_{T2}$ has reached a second time t2 ($=j_{max}/f_P$) longer than the first time t1 ($=i_{max}/f_P$). In step S1011, the protection circuit 17 determines that an overcurrent (that is, abnormality) has been detected. The process then advances to step S1007. In step S1007, the protection circuit 17 cuts off a current supplied from the power supply BAT and/or a current supplied to the power supply BAT by turning off the switch SP. This indicates that if the power supply BAT has been charged, the charging is stopped, whereas if the power supply BAT has been discharged, the discharging is stopped. This embodiment has exemplified the case in which the first threshold $i_{T1}$, the second threshold $i_{T2}$, $i_{max}$, and $j_{max}$ are common to a charging operation and a discharging operation. Instead of this setting, at least one of the first threshold $i_{T1}$, the second threshold $i_{T2}$, $i_{max}$, and $j_{max}$ may differ between a charging operation and a discharging operation. In addition, the sampling period $f_P$ may differ between a charging operation and a discharging operation.

Figure 11:
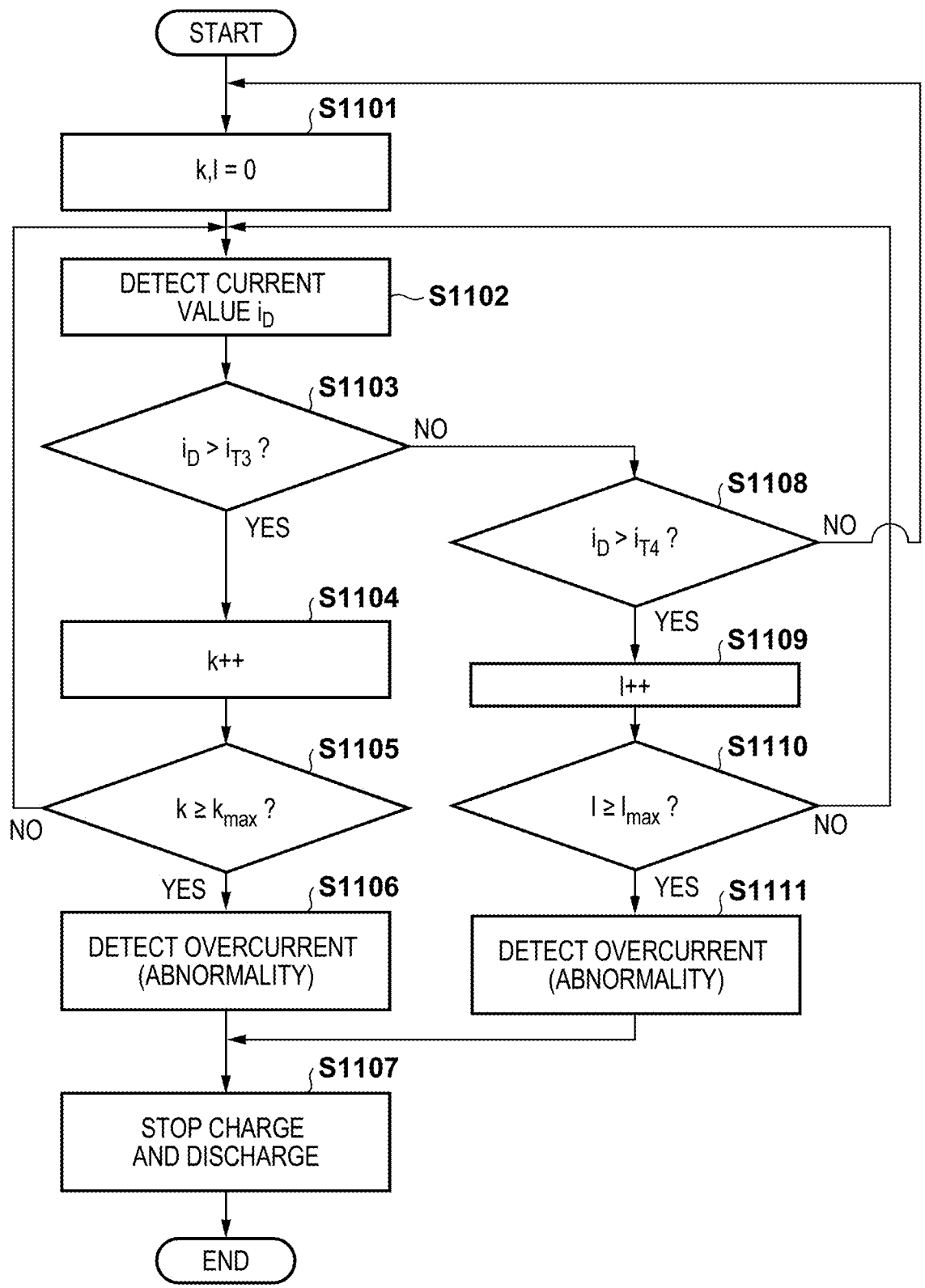
FIG. 11 is a flowchart exemplarily showing the operation of a processor associated with the protection of the power supply.

FIG. 11 exemplarily shows the operation of the processor 14. In step S1101, the processor 14 initializes the parameters k and 1 to 0. In step S1102, the processor 14 detects a current value $i_D$ (a charging current value at the time of charging or a discharge current value at the time of discharging) flowing in the power supply BAT. In the following description, the current value $i_D$ is handled as an absolute value. Note that the current value $i_D$ indicates only a positive value and its minimum value is 0 at both the time of charging and the time of discharging. In step S1103, the processor 14 determines whether the current $i_D$ exceeds a third threshold in. If YES in step S1103, the process advances to step S1104; otherwise, the process advances to step S1108. In step S1104, the processor 14 adds 1 to the value of the parameter k. In step S1105, the processor 14 determines whether the value of the parameter k is equal to or more than $k_{max}$. If the value of the parameter k is equal to or more than $k_{max}$, the process advances to step S1106; otherwise, the process returns to step S1102. In this case, that the value of the parameter k is equal to or more than $k_{max}$ indicates that the period during which the current value $i_D$ has exceeded the third threshold $i_{T3}$ has reached a third time t3 (=$k_{max}/f_D$). Note that $f_D$ is a period (sampling period) in which step S1102 is executed. In step S1106, the processor 14 determines that an overcurrent (that is, abnormality) is detected. The process then advances to step S1107.

In step S1108, the processor 14 determines whether the current value $i_D$ exceeds a fourth threshold $i_{T4}$ smaller than the third threshold $i_{T3}$. If YES in step S1108, the process advances to step S1109; otherwise, the process returns to step S1101. In step S1109, the processor 14 adds 1 to the value of the parameter 1. In step S1110, the processor 14 determines whether the value of the parameter 1 is equal to or more than $l_{max}$. If the value of the parameter 1 is equal to or more than $l_{max}$, the process advances to step S1111; otherwise, the process returns to step S1102. In this case, that the value of the parameter 1 is equal to or more than $l_{max}$ indicates that the period during which the current $i_D$ exceeds the fourth threshold $i_{T4}$ has reached a fourth time t4 (=$l_{max}/f_D$) longer than a third time t3 (=$k_{max}/f_D$). In step S1111, the processor 14 determines that an overcurrent (that is, abnormality) has been detected. The process then advances to step S1107. In step S1107, the processor 14 cuts off a current supplied from the power supply BAT and/or a current supplied to the power supply BAT. This operation can be implemented by, for example, turning off the first transistor Q3 when the power supply BAT has been charged, and can be implemented by, for example, inactivating the enable signal EN2 when the power supply BAT has been discharged. Note that the processor 14 may control the first switch Q1 and the second switch Q2 in the OFF state instead of or in addition to inactivating the enable signal EN2 as described above. This embodiment has exemplified the case in which the third threshold in, the fourth threshold $i_{T4}$, $k_{max}$, and $l_{max}$ serving as thresholds are common to a charging operation and a discharging operation. However, at least one of the third threshold $i_{T3}$, the fourth threshold $i_{T4}$, $k_{max}$, and $l_{max}$ may differ between a charging operation and a discharging operation. In addition, the sampling period $f_D$ may differ between a charging operation and a discharging operation.

Figure 12:
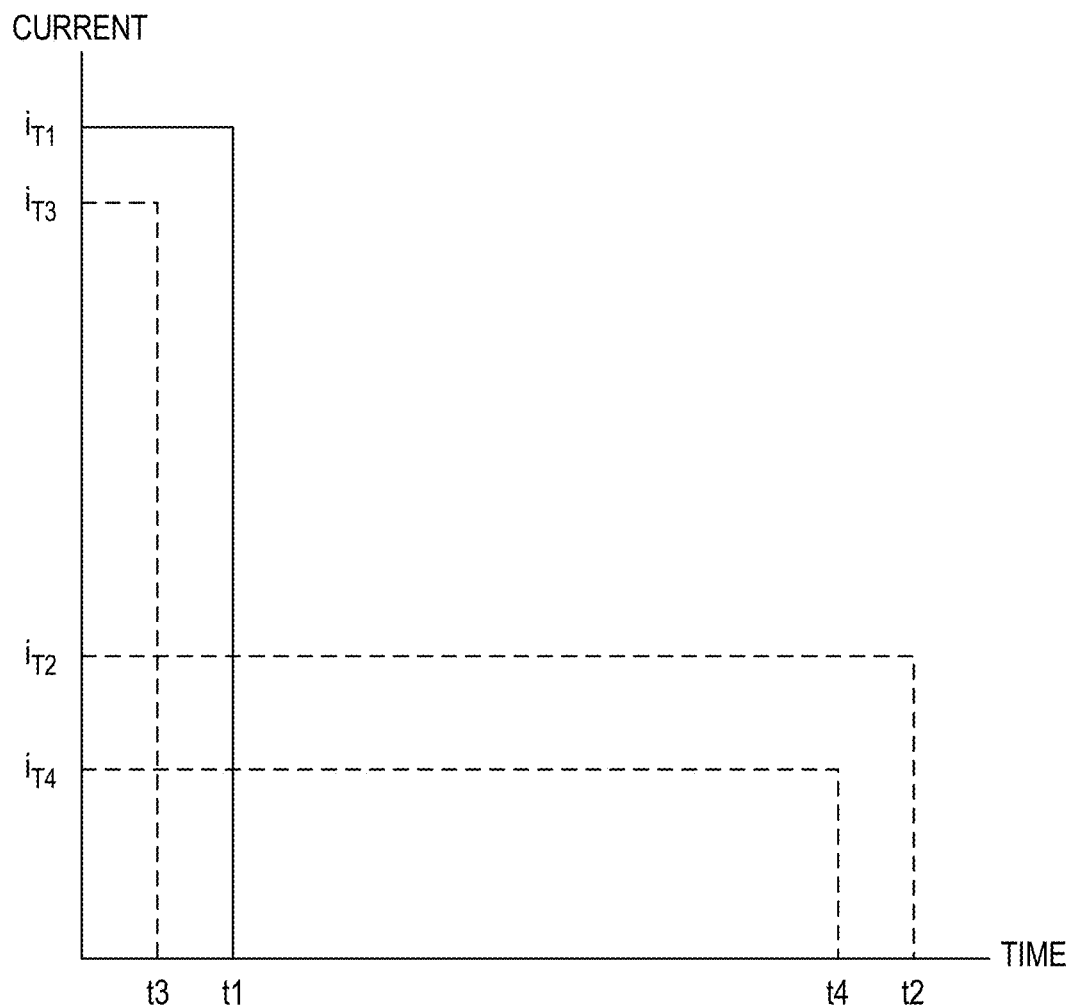
FIG. 12 is a graph exemplarily showing criteria associated with the protection of the power supply.

FIG. 12 exemplarily shows the relationship among the first threshold $i_{T1}$, the second threshold $i_{T2}$, the third threshold $i_{T3}$, the fourth threshold $i_{T4}$, the first time t1, the second time t2, the third time t3, and the fourth time t4. As described above, the first threshold $i_{T1}$, the second threshold $i_{T2}$, the first time t1, and the second time t2 are criteria based on which the protection circuit 17 determines whether to charge and discharge the power supply BAT. The third threshold $i_{T3}$, the fourth threshold $i_{T4}$, the third time t3, and the fourth time t4 are criteria based on which the processor 14 determines whether to charge and discharge the power supply BAT. The first threshold $i_{T1}$ and the first time t1 are criteria for detecting that a large current (for example, on the ampere order) flows instantaneously (for example, on the microsecond order). Likewise, the third threshold in and the third time t3 are criteria for detecting that a large current (for example, on the ampere order) flows instantaneously (for example, on the microsecond order). On the other hand, the second threshold $i_{T2}$ and the second time t2 are criteria for detecting that a small current (for example, on the sub-ampere order) flows for a long period of time (for example, on the second order). Likewise, the fourth threshold $i_{T4}$ and the fourth time t4 are criteria for detecting that a small current (for example, on the sub-ampere order) flows for a long period of time (for example, on the second order).

For example, the processor 14 determines the occurrence of abnormality in accordance with a criterion stricter than that set for the protection circuit 17. This operation can be implemented by setting the third threshold $i_{T3}$ to a value smaller than the first threshold $i_{T1}$ and larger than the second threshold $i_{T2}$, setting the fourth threshold $i_{T4}$ to a value smaller than the second threshold $i_{T2}$, setting the third time t3 to a time shorter than the first time t1, and setting the fourth time t4 to a time longer than the first time t1 and shorter than the second time t2.

According to the criteria exemplarily shown in FIG. 12, the protection circuit 17 stops the charging of the power supply BAT when the charging current value of the power supply BAT exceeds the first threshold $i_{T1}$ under monitoring over the first time t1 and when the charging current exceeds the second threshold $i_{T2}$ smaller than the first threshold $i_{T1}$ under monitoring over the second time t2 longer than the first time t1. The processor 14 also stops the charging of the power supply BAT when the charging current value exceeds the third threshold in smaller than the first threshold $i_{T1}$ and larger than the second threshold $i_{T2}$ in detection over the third time t3 shorter than the first time t1 and when the charging current exceeds the fourth threshold $i_{T4}$ smaller than the second threshold $i_{T2}$ in detection over the fourth time t4 shorter than the second time t2.

According to the criteria exemplarily shown in FIG. 12, the protection circuit 17 stops discharging from the power supply BAT when the discharge current value of the power supply BAT exceeds the first threshold $i_{T1}$ under monitoring over the first time t1 and when the discharge current value exceeds the second threshold $i_{T2}$ smaller than the first threshold $i_{T1}$ under monitoring over the second time t2 longer than the first time t1. The processor 14 also stops discharging from the power supply BAT when the discharge current value exceeds the third threshold $i_{T3}$ smaller than the first threshold $i_{T1}$ and larger than the second threshold $i_{T2}$ in detection over the third time t3 shorter than the first time t1 and when the discharge current exceeds the fourth threshold $i_{T4}$ smaller than the second threshold $i_{T2}$ in detection over the fourth time t4 longer than the first time t1 and shorter than the second time t2.

Assume that a commercially available protection IC is used as the protection circuit 17. In this case, when the first threshold $i_{T1}$, the second threshold $i_{T2}$, $i_{max}$, and $j_{max}$ in many protection ICs are changed from predetermined initial values to other values, the inside of each protection IC must be changed. Accordingly, when a commercially available protection IC is used as the protection circuit 17, there are limitations on the determination of the occurrence of abnormality according to strict criteria different from the specification of the protection IC. In contrast to this, the third threshold $i_{T3}$, the fourth threshold $i_{T4}$, $k_{max}$, and $l_{max}$ used by the processor 14 can be relatively easily changed from the write terminal of the processor 14 or the like. Accordingly, in this embodiment, the processor 14 determines the occurrence of abnormality according to strict criteria (stricter than the protection circuit 17) to improve the protection function of the inhaler 100. That the processor 14 determines the occurrence of abnormality according to criteria stricter than those in the protection circuit 17 corresponds to that the processor 14 and the protection circuit 17 independently and doubly determine the occurrence of abnormality under appropriate criteria, respectively. This also improves the protection function of the inhaler 100.

Pay attention to targets that are operated by the protection circuit 17 and the processor 14 to cut off a current supplied from the power supply BAT and/or a current supplied to the power supply BAT. As described above, the protection circuit 17 operates the switch SP to cut off a current supplied from the power supply BAT and/or a current supplied to the power supply BAT. The processor 14 operates at least one of the third voltage converter 13, the second voltage converter 12, the first switch Q1, and the second switch Q2 to cut off a current supplied from the power supply BAT. In addition, the processor 14 operates the first transistor Q3 to cut off a current supplied to the power supply BAT. As described above, the protection circuit 17 and the processor 14 operate different targets to cut off a current supplied from the power supply BAT and/or a current supplied to the power supply BAT. Under a circumstance in which an overcurrent is generated, a trouble may have occurred in any of the elements forming the electrical components 110. Assume that the protection circuit 17 and the processor 14 have respectively determined the occurrence of abnormality according to different criteria described above. Even in this case, when the protection circuit 17 and the processor 14 operate the same target, the occurrence of a trouble in the target (element) makes it difficult to properly protect the inhaler 100. Making the protection circuit 17 and the processor 14 operate different targets facilitates avoiding such a situation. This makes it possible to further improve the protection function of the inhaler 100.

The second time t2 and the fourth time t4 can be set as times longer than the time during which a current can be supplied from the power supply BAT to the heater HT in response to a first aerosol requesting operation (puff operation). Specifically, the second time t2 and the fourth time t4 can be set to times longer than the time during which the supply of a current from the power supply BAT to the heater HT is forcibly stopped even if the detection of one first aerosol requesting operation (puff operation) continues. In addition, the first threshold $i_{T1}$ and the third threshold $i_{T3}$ can be values larger than a current value flowing in the second line L2 in steps S903 to S906 in a normal state. Furthermore, the second threshold $i_{T2}$ and the fourth threshold $i_{T4}$ can be values larger than a current value flowing in the second line L2 in steps S903 to S906 in a normal state.

The invention is not limited to the foregoing embodiments, and various variations/changes are possible within the spirit of the invention.

What is claimed is:

1. An inhaler controller comprising:
    a connection terminal to which a heater configured to heat an aerosol source is connected;
    a control circuit configured to control an operation of the inhaler controller;
    a first voltage converter configured to supply a voltage to the control circuit;
    a second voltage converter configured to supply a voltage to the connection terminal;
    a power supply;
    a first power supply path configured to supply a voltage from the power supply to the first voltage converter via a first rectifier element; and
    a second power supply path configured to directly supply a voltage from the power supply to the second voltage converter by a conductive pattern,
    wherein a first period in which the first voltage converter operates is different from a second period in which the second voltage converter operates.

2. The controller according to claim 1, wherein the second period is part of the first period.

3. The controller according to claim 1, further comprising a third power supply path configured to supply a voltage from an external power supply to the first voltage converter.

4. The controller according to claim 3, wherein a voltage cannot be supplied from the external power supply to the second voltage converter.

5. The controller according to claim 1, wherein the first rectifier element includes a Schottky diode.

6. The controller according to claim 1, wherein a positive terminal of the power supply is electrically connected to the second voltage converter via the second power supply path.

7. The controller according to claim 1, further comprising a regulator configured to supply a voltage to the connection terminal so as to cause the heater to heat the aerosol source.

8. The controller according to claim 1, wherein the number of loads connected to an output terminal of the first voltage converter is larger than the number of loads connected to an output terminal of the second voltage converter.

9. The controller according to claim 1, wherein total power consumption of the loads connected to the output terminal of the first voltage converter is smaller than total power consumption of the loads connected to the output terminal of the second voltage converter.

10. The controller according to claim 1, wherein self-current consumption of the first voltage converter is smaller than self-current consumption of the second voltage converter.

11. The controller according to claim 1, wherein a load transient response characteristic of the second voltage converter is better than a load transient response characteristic of the first voltage converter.

12. An inhaler controller comprising:
a connection terminal to which a heater configured to heat an aerosol source is connected;
a control circuit configured to control an operation of the inhaler controller;
a first voltage converter configured to supply a voltage to the control circuit;
a second voltage converter configured to supply a voltage to the connection terminal;
a power supply;
a first power supply path configured to supply a voltage from the power supply to the first voltage converter;
a second power supply path configured to supply a voltage from the power supply to the second voltage converter; and
a third power supply path configured to supply a voltage from an external power supply to the first voltage converter,
wherein a first period in which the first voltage converter operates is different from a second period in which the second voltage converter operates,
wherein a first rectifier element is arranged in the first power supply path, a voltage being supplied from the power supply to the first voltage converter via the first rectifier element, and
wherein a first transistor is connected in parallel with the first rectifier element.

13. The controller according to claim 12, wherein the first transistor includes a first body diode, and
a forward direction of the first body diode is the same as a forward direction of the first rectifier element.

14. The controller according to claim 12, wherein the power supply is charged by the external power supply via the first transistor.

15. The controller according to claim 12, wherein a second rectifier element is arranged in the third power supply path, and a voltage is supplied from the external power supply to the first voltage converter via the second rectifier element.

16. The controller according to claim 12, wherein
a second rectifier element is arranged in the third power supply path, and a voltage being supplied from the external power supply to the first voltage converter via the second rectifier element, and
the second rectifier element includes a second body diode included in a second transistor arranged in the third power supply path.

17. The controller according to claim 16, wherein a source of the first transistor is electrically connected to a source of the second transistor.

18. The controller according to claim 16, wherein a source of the first transistor, a source of the second transistor, and a power supply terminal of the first voltage converter are electrically connected to each other.

19. The controller according to claim 16, wherein the power supply is charged by the external power supply via the first transistor and the second transistor.

20. The controller according to claim 12, wherein the first rectifier element includes a Schottky diode.

* * * * *